US011951039B2

(12) United States Patent
Litherland et al.

(10) Patent No.: US 11,951,039 B2
(45) Date of Patent: Apr. 9, 2024

(54) DEVICES AND METHODS FOR TREATING EYELIDS

(71) Applicant: eyeThera LLC, Kennebunk, ME (US)

(72) Inventors: Craig Michael Litherland, Denver, CO (US); Edward Jaccoma, Fairfield, CT (US); Andrew Jaccoma, Belmont, MA (US)

(73) Assignee: eyeThera LLC, Kennebunk, ME (US)

( * ) Notice: Subject to any disclaimer, the term of this patent is extended or adjusted under 35 U.S.C. 154(b) by 850 days.

(21) Appl. No.: 16/610,888

(22) PCT Filed: May 7, 2018

(86) PCT No.: PCT/US2018/031294
§ 371 (c)(1),
(2) Date: Nov. 4, 2019

(87) PCT Pub. No.: WO2018/204903
PCT Pub. Date: Nov. 8, 2018

(65) Prior Publication Data
US 2020/0069468 A1    Mar. 5, 2020

Related U.S. Application Data

(60) Provisional application No. 62/572,307, filed on Oct. 13, 2017, provisional application No. 62/502,081, filed on May 5, 2017.

(51) Int. Cl.
*A61F 9/007* (2006.01)
*A61B 90/00* (2016.01)
(Continued)

(52) U.S. Cl.
CPC .......... *A61F 9/00772* (2013.01); *A61B 90/04* (2016.02); *A61F 9/00745* (2013.01);
(Continued)

(58) Field of Classification Search
CPC .. A61F 9/007; A61F 9/00718; A61F 9/00772; A61F 9/0079; A61F 2009/00861;
(Continued)

(56) References Cited

U.S. PATENT DOCUMENTS

| 2,283,752 A | 5/1942 | Gonsett |
| 4,570,626 A | 2/1986 | Norris et al. |

(Continued)

FOREIGN PATENT DOCUMENTS

| EP | 2056753 B1 | 6/2016 |
| KR | 101714710 B1 | 3/2017 |

(Continued)

OTHER PUBLICATIONS

International Search Report and Written Opinion of PCT/US2018/031294 dated Dec. 14, 2018.

(Continued)

*Primary Examiner* — Ahmed M Farah

(57) ABSTRACT

An ocular protection device and treatment methods are disclosed. The device has a corneal shield with an attached handle. The handle may be used to move the corneal shield to better protect the eye from various treatment modalities. The handle may also be used to place tension on the eyelid to counteract the forces imposed by a treatment handpiece. A procedure for treating the eye is disclosed where multiple passes with a treatment handpiece cause a gradual increase in the temperature of an eyelid up to a treatment temperature. Once the treatment temperature has been met, occlusions in the Meibomian glands of the eyelid may be expressed. The procedure may be repeated recursively until a desired level of expression has been achieved.

19 Claims, 20 Drawing Sheets

(51) Int. Cl.
*A61B 17/00* (2006.01)
*A61B 18/08* (2006.01)
*A61B 18/12* (2006.01)
*A61F 9/008* (2006.01)

(52) U.S. Cl.
CPC .. *A61F 9/0079* (2013.01); *A61B 2017/00057* (2013.01); *A61B 2017/00084* (2013.01); *A61B 2017/00424* (2013.01); *A61B 18/08* (2013.01); *A61B 18/12* (2013.01); *A61B 2090/0436* (2016.02); *A61B 2090/0472* (2016.02); *A61B 2090/0481* (2016.02); *A61B 2090/049* (2016.02); *A61F 2009/00861* (2013.01)

(58) Field of Classification Search
CPC ........... A61F 2009/00885; A61B 90/04; A61B 2090/0436; A61B 2090/0472; A61B 2090/0481; A61B 2090/049; A61B 18/04; A61B 18/08; A61B 18/012; A61B 2017/00084; A61B 2017/00088; A61B 2017/00092; A61B 2017/00106; A61B 2017/0042; A61B 2017/00424
USPC .............. 606/4–6; 607/88, 89, 96, 100–102; 128/898
See application file for complete search history.

(56) References Cited

U.S. PATENT DOCUMENTS

| | | | |
|---|---|---|---|
| 5,487,394 | A | 1/1996 | Shiu et al. |
| 5,918,600 | A | 7/1999 | Durette |
| 7,188,625 | B2 | 3/2007 | Durette |
| 7,981,145 | B2 | 7/2011 | Korb et al. |
| 7,981,146 | B2 | 7/2011 | Korb et al. |
| 8,128,674 | B2 | 3/2012 | Korb et al. |
| 8,667,612 | B2 | 3/2014 | Fr?hlich et al. |
| 8,950,405 | B2 | 2/2015 | Grenon et al. |
| 9,463,201 | B2 | 10/2016 | Alster et al. |
| 9,763,827 | B2 | 9/2017 | Kelleher et al. |
| 2004/0237969 | A1 | 12/2004 | Fuller |
| 2006/0243286 | A1 | 11/2006 | Durette |
| 2008/0109052 | A1 | 5/2008 | Grenon et al. |
| 2008/0114421 | A1 | 5/2008 | Korb et al. |
| 2008/0114424 | A1 | 5/2008 | Grenon et al. |
| 2008/0114427 | A1 | 5/2008 | Korb et al. |
| 2008/0132978 | A1 | 6/2008 | Korb et al. |
| 2012/0111339 | A1* | 5/2012 | Barthe ...................... A61B 3/00 128/846 |
| 2014/0135784 | A1* | 5/2014 | Maroscheck ......... A61F 2/1678 606/107 |
| 2015/0000674 | A1 | 1/2015 | Barthe et al. |
| 2015/0005750 | A1 | 1/2015 | Kelleher et al. |
| 2015/0057701 | A1 | 2/2015 | Kelleher et al. |
| 2015/0148711 | A1* | 5/2015 | Bujak ..................... A61F 9/007 601/2 |
| 2015/0320590 | A1 | 11/2015 | Whitehurst et al. |
| 2016/0367398 | A1 | 12/2016 | Morgan et al. |
| 2017/0071790 | A1* | 3/2017 | Grenon .................... A61F 7/12 |
| 2017/0087009 | A1* | 3/2017 | Badawi ................ A61K 8/0208 |
| 2020/0179168 | A1* | 6/2020 | Kelleher .............. A61N 5/0624 |

FOREIGN PATENT DOCUMENTS

| | | |
|---|---|---|
| WO | 2005053585 A1 | 6/2005 |
| WO | 2008039221 A1 | 4/2008 |
| WO | 2008085162 A1 | 7/2008 |
| WO | 2008089327 A1 | 7/2008 |
| WO | 2016022596 A1 | 2/2016 |
| WO | 2017100608 A1 | 6/2017 |

OTHER PUBLICATIONS

Craig, J.P., et al., "Tear Lipid Layer Structure and Stability Following Expression of the Meibomian Glands," Ophthal. Physiol. Opt. vol. 15, No. 6, 1995, pp. 569-574.

Paugh, J.R. et al., "Meibomian Therapy in Problematic Contact Lens Wear," Entrez PubMed, Optom Vis Sci. Nov. 1990; 68(11): 803-6, 1 page.

Korb, Donald R. et al., "Increase in Tear Film Lipid Layer Thickness Following Treatment of Meibomian Gland Dysfunction" Lacrimal Gland, Tear Film and Dry Eye Syndromes: Basic Science Clinical Relevance. Adv. Exp. Med. Biol., vol. 350, 1994, 6 pages (pp. 293-298).

\* cited by examiner

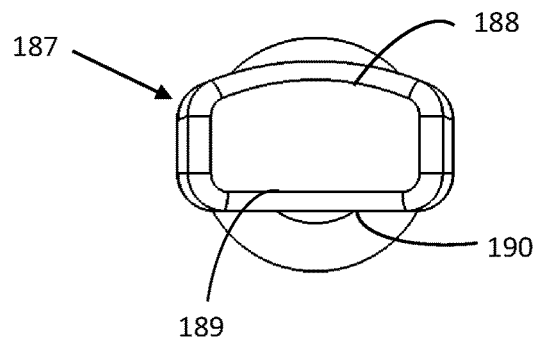
FIG. 15
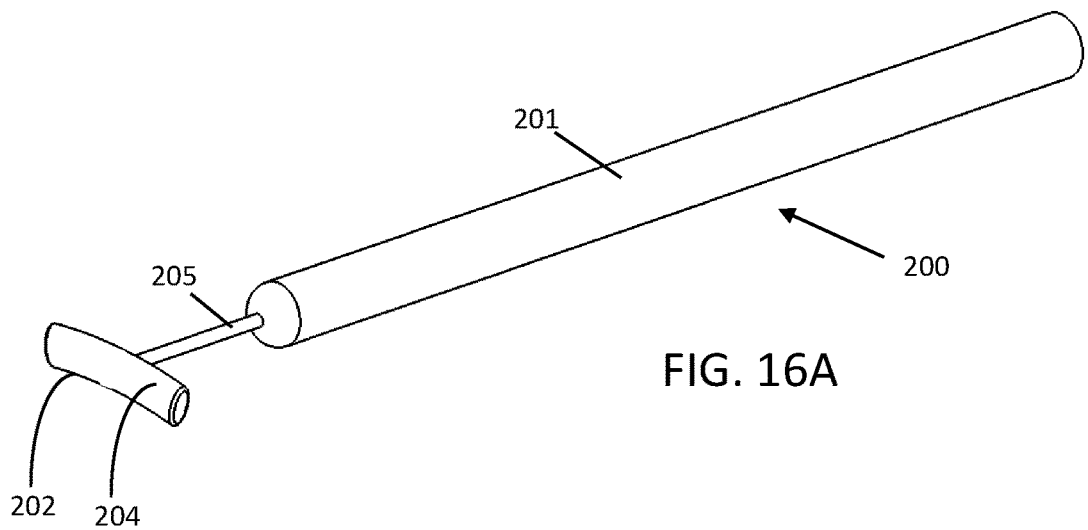
FIG. 16A
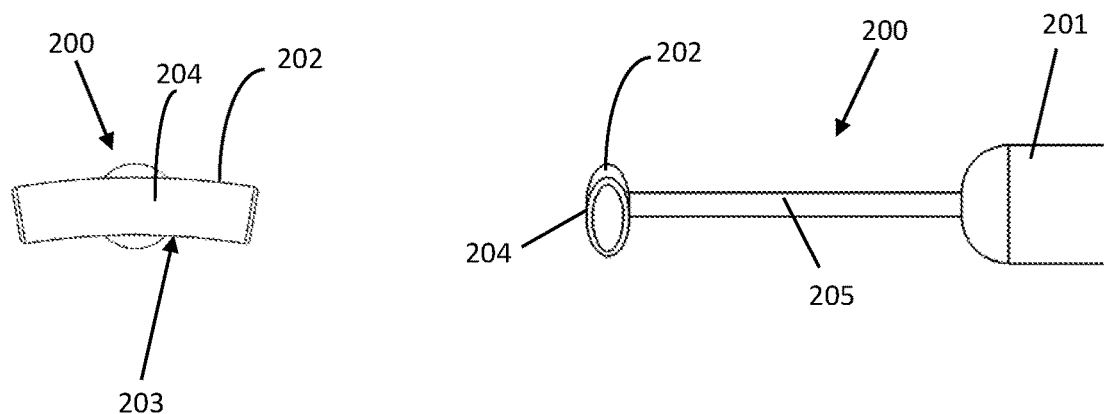
FIG. 16B
FIG. 16C

DEVICES AND METHODS FOR TREATING EYELIDS

CROSS-REFERENCE TO RELATED APPLICATIONS

This application is a national stage filing of International Application No. PCT/US2018/031294, filed May 7, 2018, the entirety of which is hereby incorporated herein by reference. This application also claims the benefit and priority of U.S. Provisional Application Ser. No. 62/502,081, filed on May 5, 2017, and U.S. Provisional Application Ser. No. 62/572,307, filed on Oct. 13, 2017, both of which are hereby incorporated by reference in their entireties.

TECHNICAL FIELD

This disclosure relates to methods and devices for use in ophthalmology, more particularly, to methods and devices for treating eyelids with the use of an ocular protection device.

BACKGROUND

Corneal shields may be used to protect the eye during procedures on and around the eyelids such as in aesthetic procedures. Such procedures typically involve the use of lasers, electrocautery instruments, radio frequency devices, or heating elements that require that the eye is physically protected during the procedure. Corneal shields may be made of metal or plastic. Metal shields are often, but not exclusively, used for light and laser procedures while plastic shields are typically used in radio frequency or thermal conduction procedures.

Corneal shields are inserted by lifting the eyelid and placing the shield directly onto the eye underneath the eyelids. The inner (eye-contacting) surface of the shield has a smooth surface to reduce the risk of damage to the eye, and some shields are vaulted to alleviate pressure over the cornea. These devices may be removed from under the eyelids by a suction device that can adhere to the surface of the shield to extract it from the eye.

Other corneal shields may be removed by a short tab or pin (U.S. Pat. No. 6,123,081) attached to the shield or a short wedge that can be grasped with forceps such as in the Crouch™ Corneal Protector. In the latter, the tab or wedge is designed to sit between the eyelids as they close upon it, such that it protrudes between the lid margins.

Procedures involving the application of pressure directly around the eyelids are increasingly common and are often aimed at treating wrinkles or heating the meibomian glands in patients with dry eye disease. In some procedures, pressure is applied to the eyelid via a treatment device (handpiece) while heat is applied through the device onto the eyelid and the surrounding orbital areas. In other approaches, the lid may be treated initially with a laser or other light source, then massaged with another device afterward. The operator may apply a massaging motion around the outer surface of the eyelid using the tip of a handpiece. A corneal shield may be in place to protect the eye.

Massaging on the eyelids tends to irritate the eye because the force applied to the eyelid is transmitted to the corneal shield, which in turn transmits the force to the eye. These forces can cause retropulsion of the eye as well as migration of the corneal shield on the eye because the shield is free to float on the eye. For the patient, this may cause pain and redness, or even scratches on the cornea.

There is, therefore, a need for a comfortable shield that protects the eye from energy and forces applied during eyelid treatments.

SUMMARY

The present disclosure is directed to devices and methods for treating eyelids to remove obstructions located in the Meibomian glands while protecting the eye. Various medical and aesthetic devices are used on the face and around the eyes; some of these devices apply energy that heats tissue and may be used on the eyelids to heat the Meibomian glands residing therein, to melt, loosen, or soften obstructions in the glands. During such procedures, the eye may be protected. That is, the eye may be shielded from the energy and force that is directed into the eyelid. While an operator manually treats the eyelid, the forces on the eyelid may cause a conventional corneal shield to move around on the eye and to transmit the forces applied to the lids to the eye, potentially causing pain, irritation, or retropulsion.

In this regard, embodiments disclosed herein include methods and devices to manually treat Meibomian gland dysfunction while manually controlling a corneal shield. An embodiment includes an ocular protection device comprising a corneal shield configured to fit underneath eyelids, the corneal shield having a sufficiently smooth inner surface to prevent damage to an eye and a handle rigidly connected to the outer surface of the corneal shield so that it may protrude between closed eyelids.

The handle may be sufficiently long to allow an operator to control the corneal shield via the handle while having an unobstructed view and access to the eyelids during treatment of the eyelid. The length of the handle may be at least 30 mm in length, and it may be integrally formed with the shield such as by 3D printing or injection molding. It may have a mechanical or living hinge that may be offset from the surface of the corneal shield, for example, by greater than about 15 mm. The handle may have a junction piece that joins sections of the handle together; the junction piece may overmolded, and it may include a living hinge to allow the operator to move his or her hand and the handle out of the way. Additionally, the handle may have an appendage near its proximal end for manipulating with the hand. The handle may be made of a metal or a polymer such as Nylon, ABS, PMMA, PEEK, polyethylene, and polypropylene and it may be overmolded with an elastomeric material such as rubber, silicone, or a thermoplastic elastomer (TPE).

The corneal shield may comprise a material that substantially insulates against electrical and thermal energy to protect the eye; for example, it may be made of a polymeric material such as Nylon, ABS, PMMA, PEEK, polyethylene, and polypropylene. The shield may be made of a material that substantially blocks light from IPL handpieces which, for example, may have a wavelength of about 500 nm to about 1200 nm.

In another embodiment, an ocular protection device may comprise a corneal shield and a handle rigidly connected to the outer surface of the corneal shield; the handle configured to protrude between closed eyelids so that it may be handled by the operator. To allow the operator to control the shield while keeping his or her hands clear of the treatment area (the eye), the proximal end of the handle may extend laterally beside the eye so that a hand grasping the handle is clear of the front of the eye. The handle may have an appendage at its proximal end to facilitate grasping the device, and the handle and shield may be integrally formed as a single part.

Methods described herein may be performed with devices according to embodiments disclosed herein. For example, a method for treating Meibomian gland dysfunction comprises shielding the surface of the eye using an ocular protection device having a corneal shield and a handle which allows for manipulation of the corneal shield on the eye, heating the eyelid using a treatment handpiece to a temperature to melt, soften, or loosen obstructions in the Meibomian glands, then applying pressure to the outer surface of the eyelid to express obstructions blocking the glands, and controlling the corneal shield, via the handle, to apply a counterforce to the applied pressure. The eyelid may be heated by any technology that provides an adequate increase in eyelid temperature, for example, to achieve a temperature between 37° C. and 48° C. Examples of technologies that may be used to heat the eyelid include radio frequency energy (RF), intense pulsed light (IPL), thermal conduction, and ultrasonic vibrations. The applied pressure is in a range of about 0.5 psi to about 10 psi and may be applied in strokes toward the lid margin. The temperature of the eyelid may be measured using a temperature sensor, such as, an infrared temperature sensor, a fiber optic sensor, a thermistor, or a thermocouple; the temperature sensor may be attached to the handpiece. The temperature may be automatically controlled via feedback control.

During procedures, the handle may be flexed to an angle of at least 30° from its neutral axis to permit access to the eyelid. Flexing may be accomplished by a hinge which permits movement of the handle to allow access to the eyelid while also allowing the operator to control the corneal shield. The pressure may be applied by the handpiece, by a separate expressor, or by an expressor attached to the handpiece.

In another embodiment, an ocular protection device may have a generally concave corneal shield configured to fit on the eye surface. The shield may be made of a thermoplastic material having a flexural modulus of about 0.4 to about 5 GPa, as measured in accordance with ASTM D790, and it may have an eye-contacting surface sufficiently smooth to prevent damage to the eye. A handle may be attached to the corneal shield for manipulation and control of the shield about the eye surface. The handle may flex at least 30° from its neutral axis under a force of about 0.5N or less. The shield and the handle may be joined by a mechanical joint, a press-fit, an overmold, a solvent bond, a hot-melt joint, or an adhesive joint, for example. The shield may include an integrally formed stem portion for connecting to the handle.

In another embodiment, a method of treating dry eye syndrome may include shielding the surface of the eye using an ocular device having a shield and a handle which allows for manipulation of the shield on the eye and application of tension to the inside of the eyelid. Heat is applied to the eyelid surface overlying the Meibomian glands; the heat may be slowly increased until the eyelids reach a temperature of between 40° C. and 48° C. A massaging pressure is applied to the eyelid surface overlying the Meibomian glands while an opposing tension is applied to the underside of the eyelid using the device to facilitate expression of material blocking the glands.

The heat in the eyelid may be created by applying one of radio frequency (RF) energy, thermal energy, or microwave energy for about 10 seconds to about 15 minutes. The messaging pressure may be about 0.5 psi to about 10 psi. in massaging motions applied toward the eyelid margin for about 10 seconds to about 1 minute per eyelid. During treatment, the handle of the device can be flexed to an angle of at least 30° from its neutral axis to permit a clear view of the eyelid. Flexing may be afforded by a hinge which permits movement of the handle to allow a clear view of the eyelid and to allow the operator to control the corneal shield. The hinge may be a living hinge. The device may include a breakaway handle to prevent damage to eye tendons.

In another embodiment, an ocular protection device comprising a corneal shield configured to fit underneath eyelids having a sufficiently smooth inner surface to prevent damage to an eye is disclosed. The device includes a handle rigidly connected to an outer surface of the corneal shield with an integrally formed living hinge that is between about 15 mm and 30 mm from the corneal shield. The device may be fabricated as a single injection molded part and it may be made of polypropylene.

The following detailed description and drawing figures illustrate the embodiments and further aspects.

BRIEF DESCRIPTION OF THE DRAWINGS

The foregoing will be apparent from the following the more particular description of example embodiments, as illustrated in the accompanying drawings in which like reference characters refer to the same parts throughout the different views. The drawings are not necessarily to scale, emphasis instead being placed upon illustrating embodiments of the present invention.

FIG. 15 is an end-view of a handpiece tip with a curved edge.

FIGS. 16A-16C show various views of an eyelid expressor.

DETAILED DESCRIPTION

A description of example embodiments follows. Like numbers refer to like elements throughout.

While this invention has been particularly shown and described with references to example embodiments thereof, it will be understood by those skilled in the art that various changes in form and details, as well as permutations and combinations, may be made without departing from the scope of the invention encompassed by the appended claims. Rather, these embodiments are provided for illustrative purposes and are not intended to be limiting in any way.

For this disclosure, the term proximal and distal are used with reference to the device being described, that is, proximal is generally closer to the handle/operator of the device or handpiece and distal is toward the end of the device near the patient. As the procedures described herein are manual procedures, the operator may use one or both hands while performing the methods. For purposes of illustration, in this disclosure the operator's treatment hand 1 (e.g., in FIG. 1) refers to the hand that is holding a handpiece (i.e. treatment device) while the operator's protection hand 2 (e.g., in FIG. 8B) refers to the hand that is controlling the ocular protection device. One skilled in the art will recognize that either hand may be used for holding either device and that devices may be switched between hands throughout the procedure depending on convenience, which eye is being treated, the operator's handedness, or other factors. In addition, the methods disclosed herein may be conducted by more than one operator. For example, one operator may control a handpiece while another operator controls an ocular protection device. Furthermore, one or more operators may control a handheld thermal sensing camera or other device for imaging the patient's eyelid during a procedure.

Figure 1:
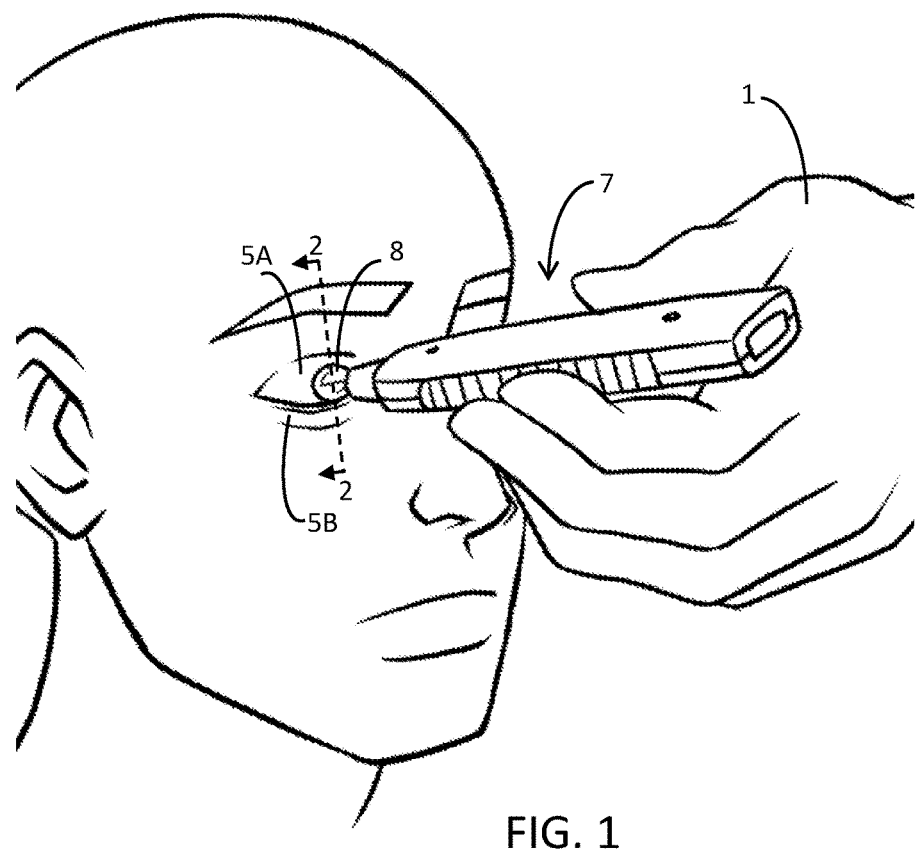
FIG. 1 is a perspective view showing an upper eyelid being treated by a handpiece.

FIG. 1 illustrates a handpiece 7 used to treat an upper eyelid 5A using a corneal shield (under the eyelid). The operator's treatment hand 1 holds the handpiece 7 having a tip 8 that applies energy the upper eyelid 5A using a massaging motion while applying pressure throughout the portion of the eyelid to be treated. The handpiece 7 may be connected to an energy source such as, but not limited to, a radio frequency (RF) generator or it may be a self-contained unit. The type of energy transmitted to the eyelid may be thermal, such as conduction or convection, infrared (IR), RF electrical energy which may be mono- or bipolar, light or laser, ultrasound or any other type of energy that can affect the tissue, collagen, or Meibomian glands in the eyelids. The RF energy may be in the low frequency of less than 1 kHz, or about 400-600 kHz or the higher frequency range (e.g., 1 MHz, or for example, 2-4 MHz) used in aesthetic procedures.

The upper eyelid 5A is shown being treated with a handpiece 7 in FIG. 1, and a protective corneal shield is installed over the eye and underneath the eyelids 5A and 5B; the shield cannot be seen in the figure because it is behind the eyelids 5A and 5B, which are closed during treatment. The dashed line 2-2 in FIG. 1 indicates a cross-sectional plane through which a sectional view (2-2) is illustrated, in FIG. 2, which shows the interaction between the anatomy and various components.

Figure 2:
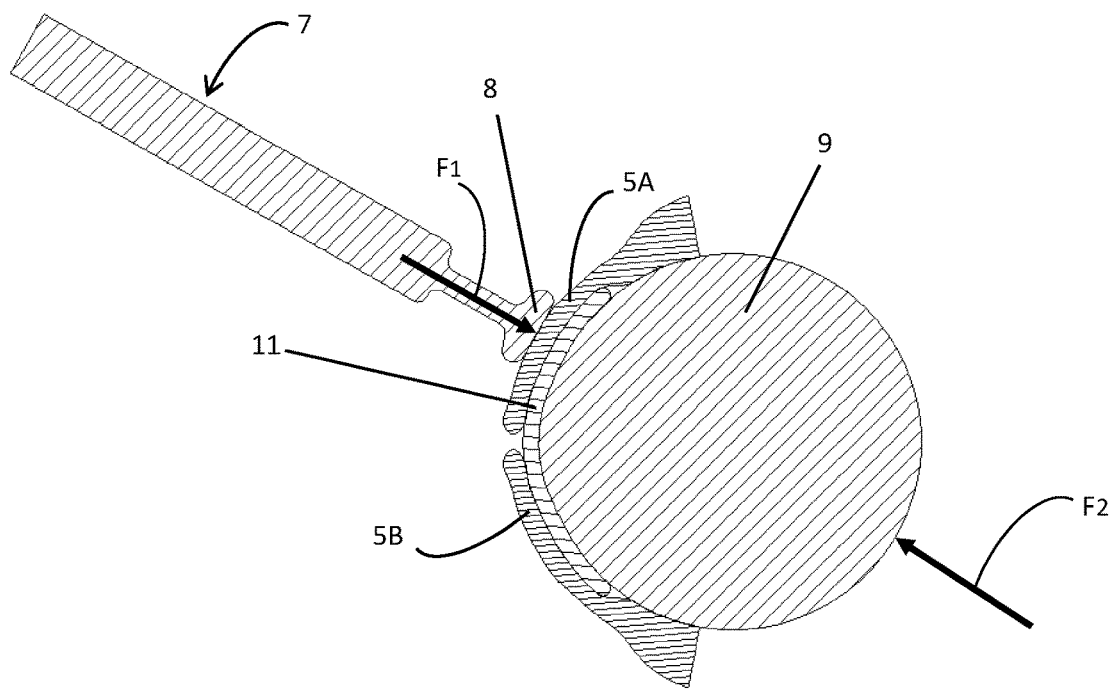
FIG. 2 is a sectional view taken from FIG. 1 showing the interface between the handpiece, an upper eyelid, a corneal shield, and an eye.

The sectional view in FIG. 2 traverses through the handpiece 7, eyelids, 5A and 5B, corneal shield 11, and eye 9. Located between the eyelids 5A and 5B and the eye 9 is the corneal shield 11, which protects the eye 9 from heat or radiation during treatments around the eyes, such as, or example, in aesthetic procedures on and around the eyelids 5A and 5B wherein the tip 8 of the handpiece 7 may be used to transmit energy to the lid. This energy and the concomitant heat generated may harm the eye 9 and associated tissues such as the cornea, conjunctiva, extraocular muscles, and sclera. In the case of laser or light therapy, the corneal shield 11 may protect the eye from transmitted light while providing aesthetic benefits to the surrounding skin such as photorejuvenation of the complexion. The corneal shield 11 may protect against electrical and thermal energy and may block the transmission of light to protect the eye.

While the present embodiment discloses a handpiece 7 that transmits RF energy, other types of treatment devices may be used, and some devices may contact the skin, or some may transmit energy to the eyelid without direct contact. In the present embodiment, since the tip 8 (electrode) creates heat by RF electrical conduction, it requires adequate contact with the skin to transfer energy to the body. This contact is achieved by the operator applying a force to the handpiece as indicated by the arrow $F_1$ which is overlaid on the handpiece 7 in FIG. 2. Some commercially available handpieces have a switch that turns on the handpiece 7 when a threshold force through the tip 8 is reached.

FIG. 2 illustrates an example of the balance of forces at an instant during treatment, for example, during the heating or expression steps of treatment as further described below. The axial force $F_1$ is transmitted through the upper eyelid 5A since it is a very thin, flexible, layup of tissues with negligible bending stiffness. The axial force further transmits through the corneal shield 11 because the shield 11, being typically comprised of plastic or metal that is about 1 mm thick, acts like a relatively rigid body floating on the eye 9; when it is pressed axially, the shield 11 tends to displace axially without deforming or otherwise resisting the net force $F_1$ because the corneal shield 11 is constrained primarily by the eye 9. Hence, the force $F_1$ is also transmitted to the eye 9, a relatively soft, aqueous-filled ellipsoid. On the opposite side of the eye 9, the force $F_1$ is transmitted from the eye 9 and reacted ($F_2$) by the surrounding anatomy that comprises the eye socket or orbit which constrains the eye 9. Hence, forces applied through the lids can push an eye 9 back, retropulsing it, so that it rests more deeply in the orbit (depressed into the orbital fat and extraocular muscles surrounding it). This, may cause discomfort or a medical problem especially if a patient has had prior surgery on the eye, rendering the wall of the eye more delicate (e.g., after a corneal transplant or glaucoma surgery—called a trabeculectomy). In those cases, it can potentially rupture and ruin an eye. Also, if a patient has advanced glaucoma, then the excess pressure caused by the force $F_1$ could conceivably cause more damage to the optic nerve—aggravating the glaucoma and damaging vision.

The reaction force $F_2$ of the anatomy supporting the eye 9 is indicated by the opposing arrow $F_2$ on the posterior of the eye 9, that is, $F_1=F_2$, approximately. Based on clinical experience, the applied pressure may be in a range of about 1 psi to 10 psi but may be as high as 30 psi (about 15N of force) or as low as 0.5 psi. By way of nonlimiting example, the pressure applied by the tip 8 of the handpiece 7 may be about 6 psi, which equates to a force of about 3 N ($F_1$).

FIGS. 1 and 2 show the handpiece tip 8 statically engaged with the upper eyelid 5A. However, during a procedure the handpiece tip 8 may not be held in one location for a long duration for several reasons: 1) the energy that is applied through the tip 8 is relatively locally concentrated at the location of the tip where it is contact with the skin, so to treat the entire eyelid it must be moved around massaging the eyelid both laterally and vertically, 2) in procedures that heat and massage the Meibomian glands, the tip 8 is dragged vertically in the direction of the glands after heating to express built up material out from the glands, and 3) leaving the tip 8 in one location may cause too much energy to be delivered to that location if the electrode is on, potentially causing a burn to the eyelid tissues. In practice, motions coupled with the applied axial force of the handpiece 7 tend to impart lateral and vertical forces to the corneal shield 11 in addition to the axial force $F_1$ described above. The forces are further illustrated in FIGS. 3 and 4 below.

Figure 3:
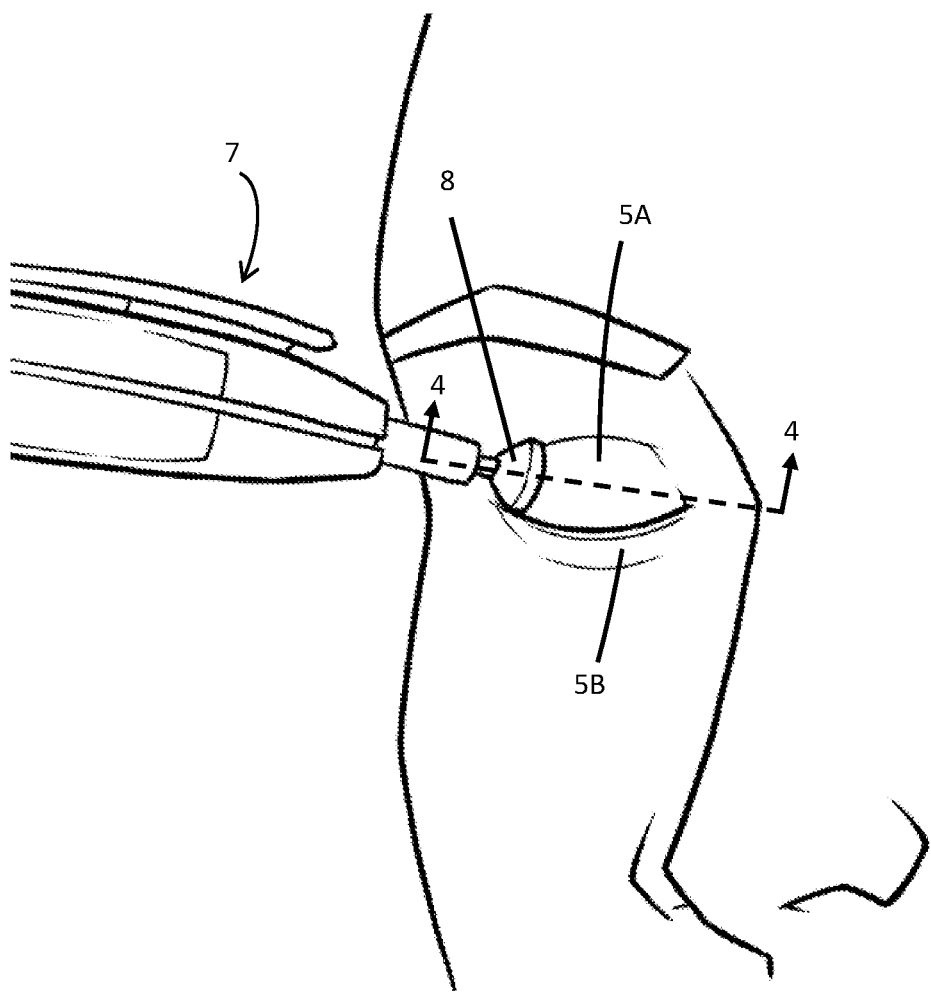
FIG. 3 is another perspective view showing an upper eyelid being treated by a handpiece.

With reference to FIG. 3, another perspective view of the treatment of an upper eyelid is illustrated. The tip 8 of the handpiece 7 is offset from the center of the upper eyelid 5A as a specific area of the eyelid 5A is being massaged. The dashed line 4-4 indicates the orientation of the sectional view that is depicted in FIG. 4; this view is looking upward and through a substantially horizontal plane through the eye 9, eyelid 5A, and handpiece 7.

Figure 4:
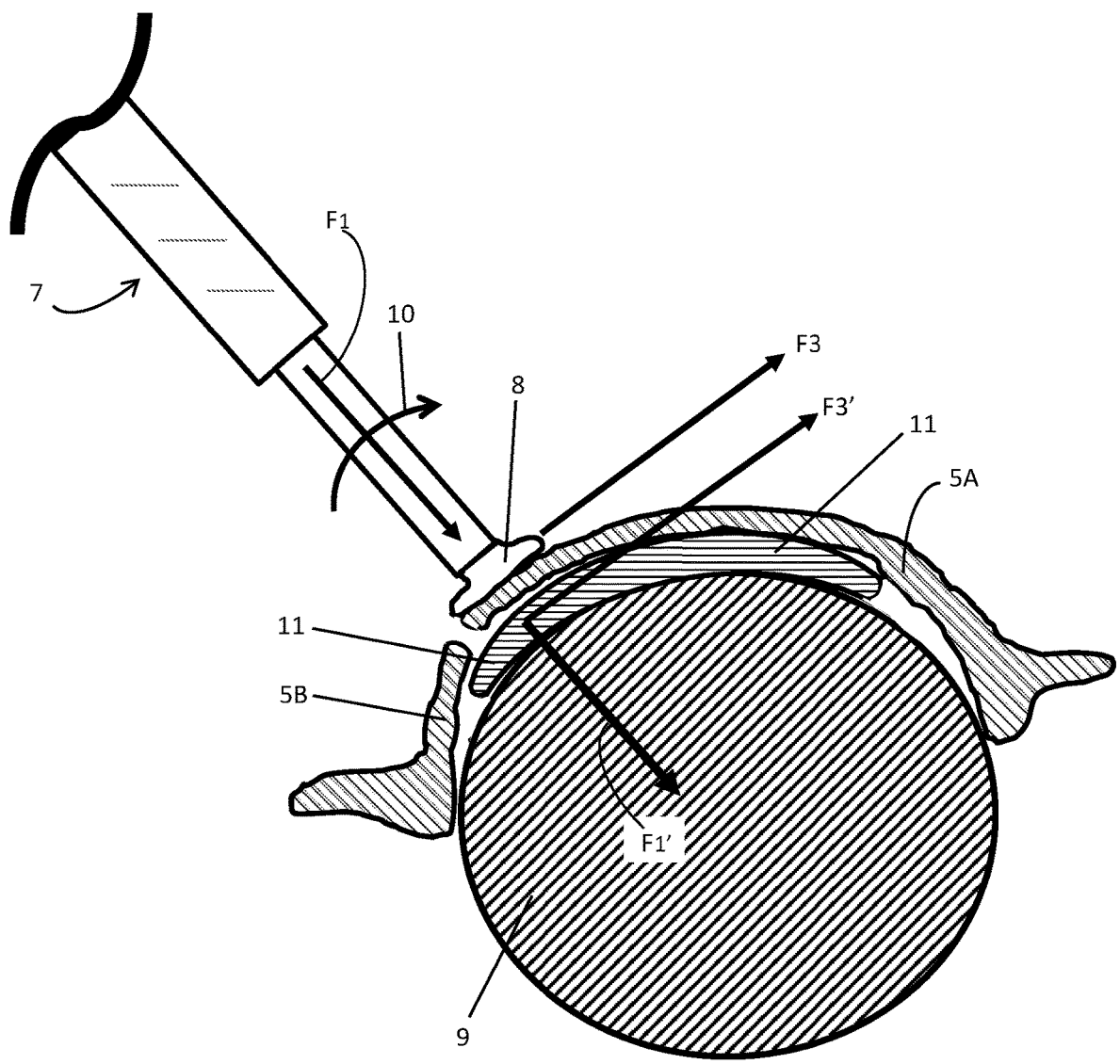
FIG. 4 is a cross-sectional view of the arrangement shown in FIG. 3 showing the interface of a handpiece, an upper eyelid, a corneal shield, and an eye.

The handpiece 7 in FIG. 4 is in motion laterally across the upper eyelid 5A as indicated by the lateral arrow 10. The operator massages the upper eyelid 5A by pressing axially on the handpiece 7 and translating it substantially laterally across the upper eyelid 5A. Hence, there are two forces incident on the eye 9 during this motion—the lateral force $F_3$ across the eyelid 5A due to the massaging motion, and the axial force $F_1$ along the handpiece 7 creating the pressure on the eye 9 described above. The latter force ($F_1$) tends to cause force ($F_{1'}$) on the eye 9 and retropulsion while the former force ($F_3$) tends to impart some amount of force ($F_{3'}$) onto the corneal shield 11 laterally that may cause the corneal shield 11 to migrate along the surface of the eye 9, as has been demonstrated in clinical experience. This combination of forces causes pain, redness, and irritation of the eye 9 and surrounding anatomy. It may also result in scratches to the cornea due to the motion of the corneal shield 11 across the eye 9. Furthermore, the shield 11 may migrate enough so as to no longer reside fully beneath the handpiece 7, thus failing to protect the eye 9. Furthermore, the misalignment may causing a high force or "pinch" on the eyelid 5A if the tip 8 is pressed over an edge of the corneal shield 11.

Figure 5A:
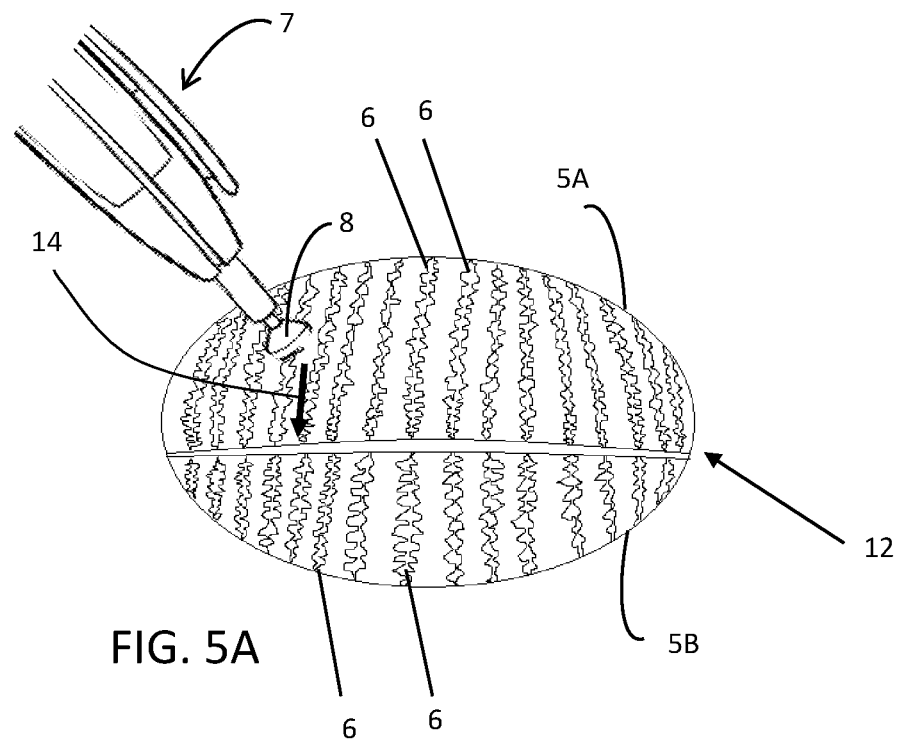
FIG. 5A is a front view of the eyelids showing Meibomian glands which reside inside of the eyelids.
Figure 5B:
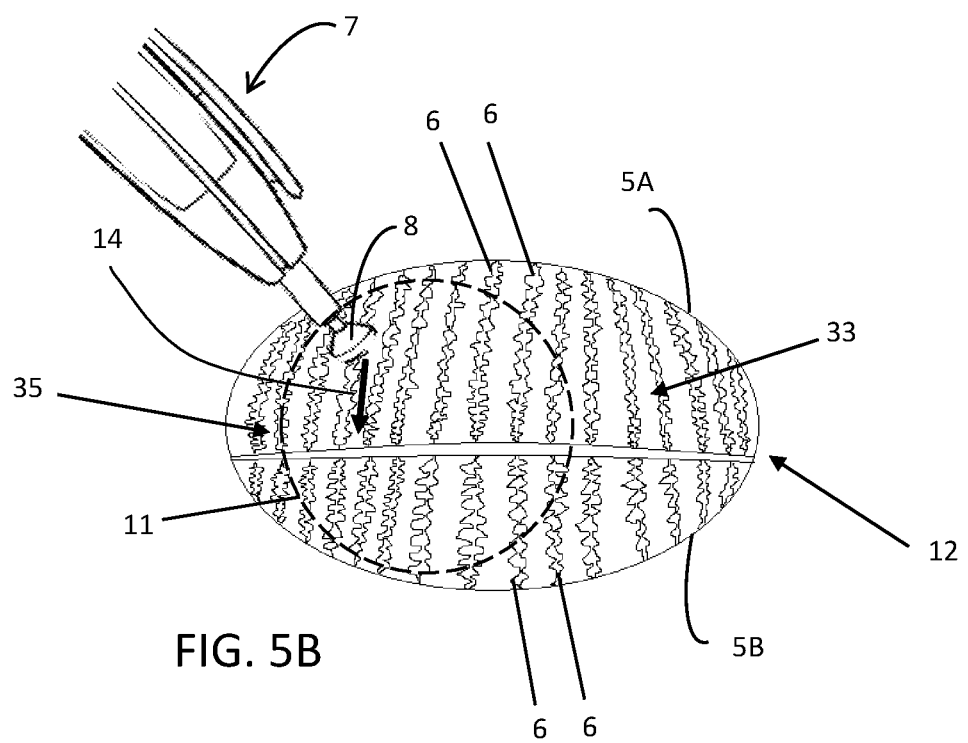
FIG. 5B is the same view as FIG. 5B, but with a circle superimposed on the eyelids representing an underlying corneal shield.

The eyelid 5A may be massaged by moving the handpiece 7 in a variety of directions so as to cover some or all of the surface of the eyelid 5A. In some instances, the operator may massage the eyelid 5A in a substantially vertical direction as shown by arrow 14 in FIG. 5A. FIGS. 5A and 5B show the handpiece tip in motion on the outer surface of the eyelid 5A while showing the orientation of the Meibomian glands 6 which reside inside of the eyelids 5A and 5B (i.e., the eyelid tissue overlaying the glands is not shown); the Meibomian glands 6 generally align with the vertical direction of the eyelids 5A and 5B. These glands 6 serve to transport oils to the surface of the eye via the lid margin 12 to create a lipid layer that tends to keep the natural fluid or tear film, on the surface of the eye from evaporating. When the Meibomian glands 6 become clogged with a wax-like substance that is substantially non-flowable or solid, the lipid layer coating the eye may be deficient leading to Meibomian Gland Dysfunction (MGD) and a type of dry eye disease called evaporative dry eye syndrome. Clearing these glands 6 of the blockages is a restorative step to regaining healthy oil production from unobstructed glands.

The wax-like substance clogging the Meibomian glands 6 may be expressed by heating it so as to melt, soften, or loosen it which may be followed by exuding or forcefully purging (expressing) it from the glands 6. For example, the handpiece 7 may be used to heat the upper eyelid 5A by massaging all around the eyelid 5A while transmitting energy. The massaging motion may be linear, circular, random, or a combination thereof; the net result is to raise the temperature of the upper eyelid 5A. Once the operator determines that the upper eyelid 5A has reached the proper temperature to melt, soften, or loosen obstruction(s) or inclusion(s) in the Meibomian glands, the glands 6 may be massaged in a generally linear fashion down the upper eyelid 5A as indicated by arrow 14. The operator repeats this procedure across the eyelid 5A, while it is in the desired temperature range, to treat the glands 6 by applying pressure only while moving down the eyelid to keep flushing the loosened material in one direction—toward the lid margin 12. The temperature of the upper eyelid 5A, may be measured by any non-contact or contacting thermal sensor, for example an infrared (IR) thermometer, fiber optic sensor, thermal imager, thermistor, resistance temperature detector (RTD), thermocouple, or an integrated silicon sensor and the sensing may be incorporated into the shield or handpiece embodiments disclosed herein. Furthermore, a thermal-sensitive shield material that changes color based on temperature may be used to indicate the temperature to the operator.

Now with reference to FIG. 5B, a dotted line is overlaid on the eyelids 5A and 5B depicting a corneal shield 11 that resides thereunder and on the eye (not shown). Due to the wide variety of anatomical eye shapes, a given corneal shield 11 may not match the lid or eye size and may result in locations where the shield 11 does not protect the eye, such as the unprotected region 33. Furthermore, clinical experience has shown that the location of the shield 11 may vary during treatment because the corneal shield 11 migrates and rotates due to the forces applied to the eyelid 5A during the procedure. That is, the tip 8 of the handpiece 7 may transmit both force and energy through the unprotected region 33 and onto the eye.

Additionally, the handpiece 7 may be used to treat glands at the periphery of the eyelid 5A and/or at the periphery of the corneal shield 11—the region designated by arrow 35. In this location, the force of the tip 8 may cause pain or a pinching sensation, or a locally concentrated heat zone because the tip 8 is pressing on the eyelid 5A over an edge of the shield 11. This is because the smaller effective contact area of the tip 8 at the edge of the shield 11 results in a higher pressure on the eyelid 5A.

Figure 6A:
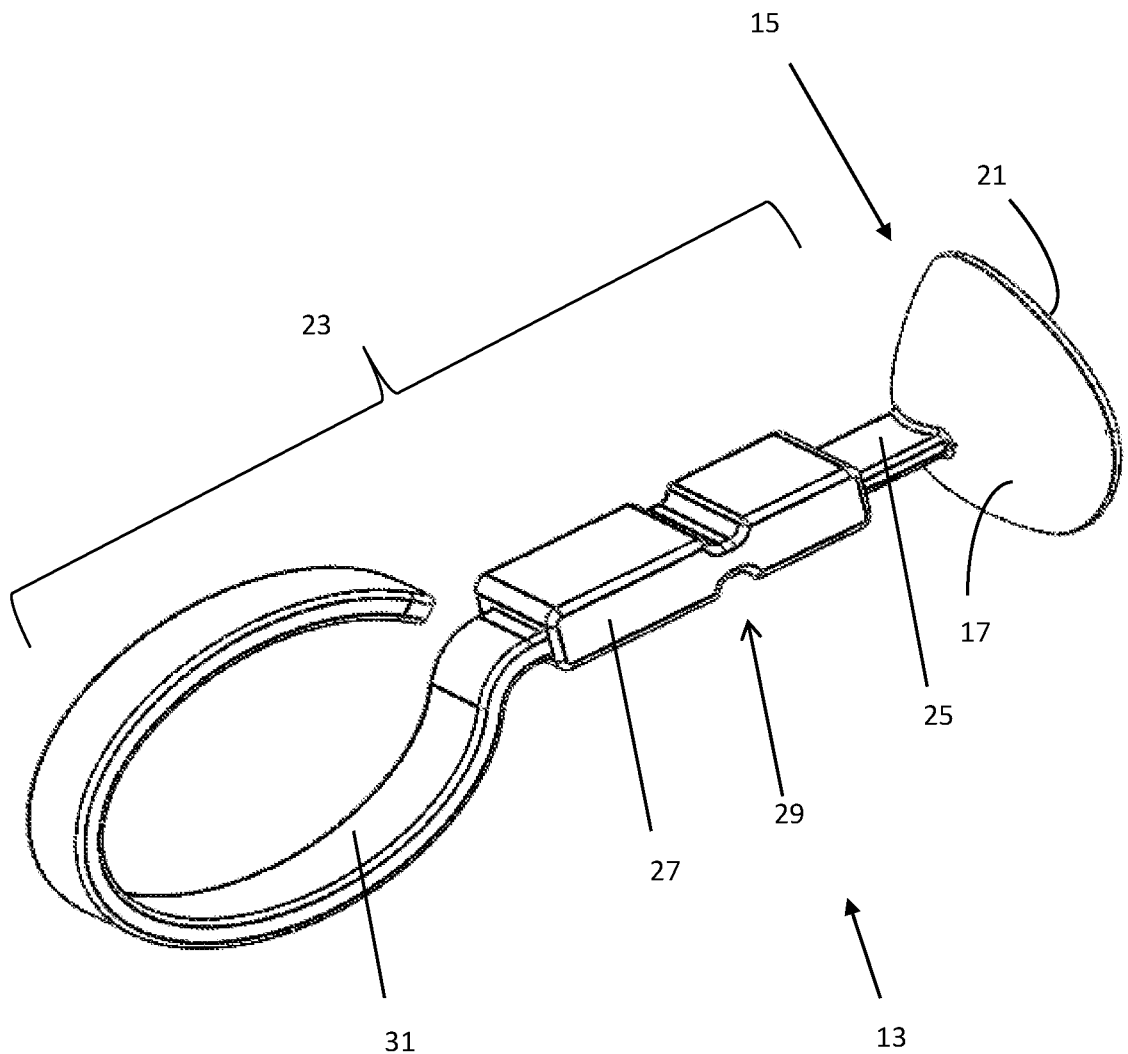
FIGS. 6A-6C are different views of an embodiment of an ocular protection device.
Figure 6B:
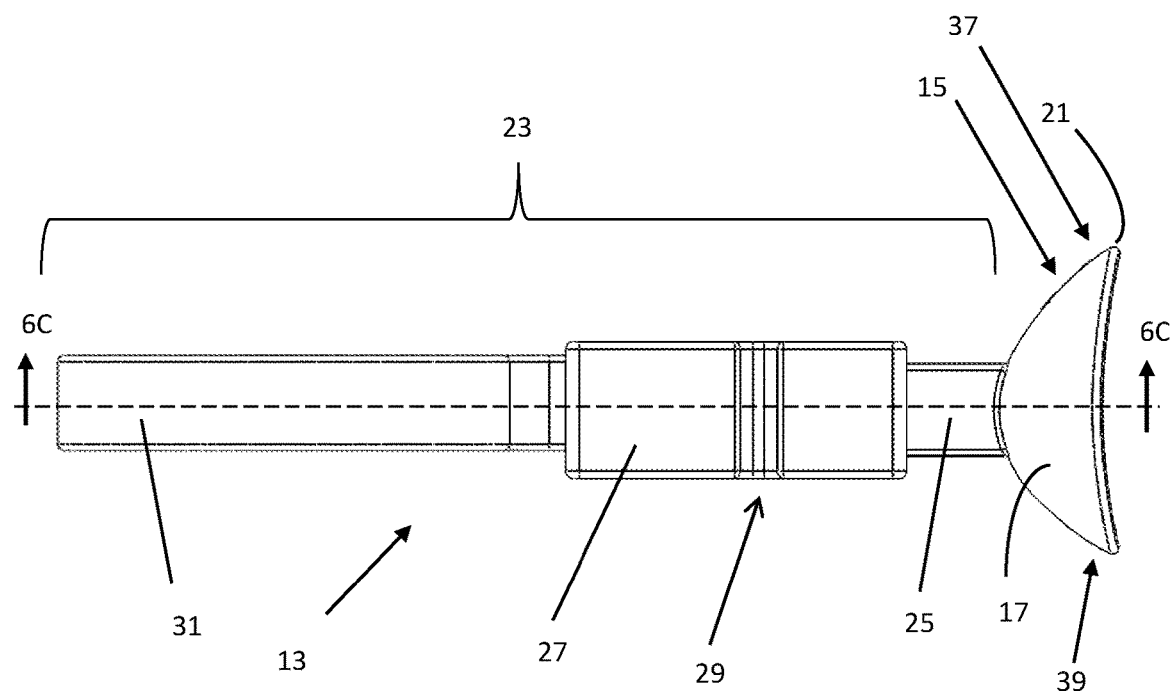
Figure 6C:
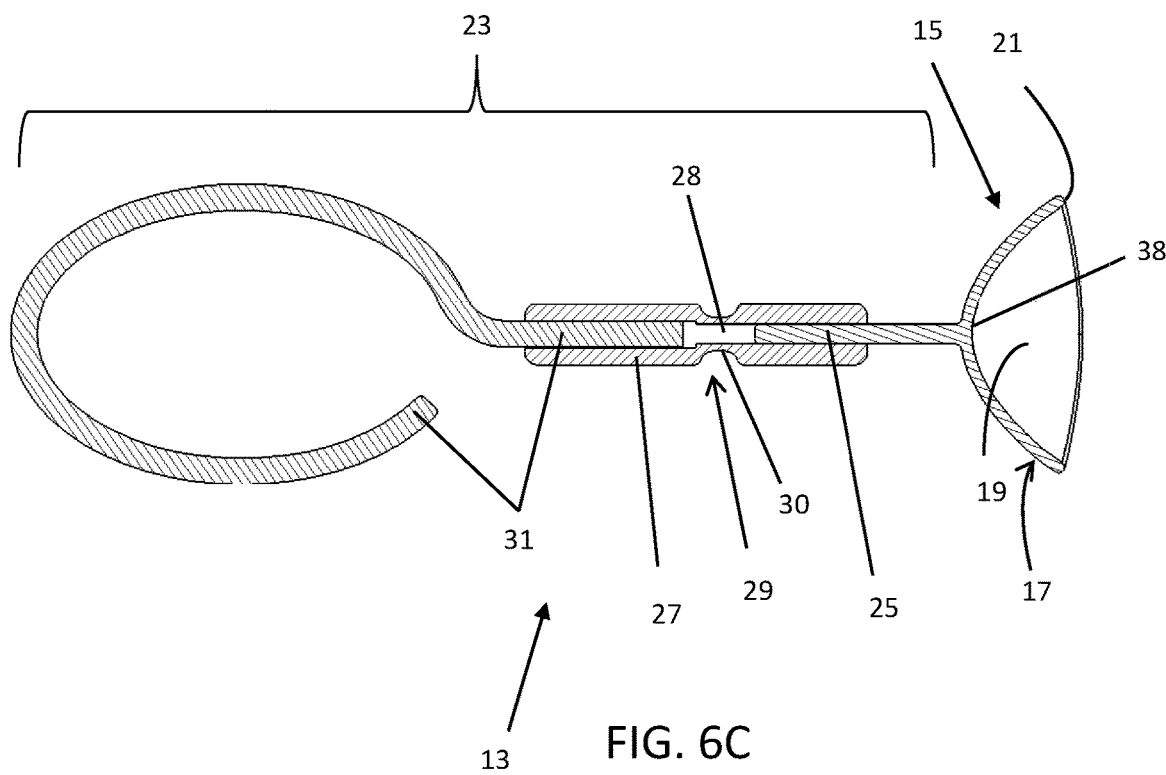

An ocular protection device is indicated by reference numeral 13 in FIGS. 6A-6C. The device 13 includes a handle 23 extending from a corneal shield 15. The corneal shield 15 may be similar to conventional corneal shields, except that it has a handle 23 attached to its proximal side 17. The handle 23 may be a one-piece shaft, or it may be comprised of multiple parts such as, but not limited to, a stem 25, a grip 27, and an appendage 31 as shown. The stem 25 emanating from the shield 15 may be integrally formed with the shield (i.e., molded), rigidly attached, or attached with a flexible joint. The stem 25 may be small in thickness, being less than about 2 mm thick, to allow the eyelids close upon it without leaving an appreciable gap between the eyelids. Otherwise, it may be of any cross-sectional shape, such round, oval, square, or rectangular, as shown in the present embodiment. The width of the stem 25 may be as wide as the eyelid margins (approximately 25 mm) or as small as about 1 mm wide or smaller as long as it has sufficient lateral stiffness and strength so that the operator may control the corneal shield 15 while treating an eyelid. For example, the operator may want to constrain the shield 15 against unwanted motion, or he or she may want to move the shield 15 to protect the eye from the pressure and/or energy applied to the eyelid.

The grip 27 may be integral to the handle 23, that is, it may be molded or machined from the same material, or it may be an overmold or press-fit, such that it is a different material than the stem 25 and appendage 31. That is, the grip 27 may be a junction between proximal and distal portions of the handle 23, such that it joins the stem 25 and appendage 31. The grip 27 may be made of a rubber-like material such as silicone, Santoprene™, or other natural or synthetic rubbers, elastomers, or polymers such as a thermoplastic elastomer (TPE). For example, the grip 27 may be composed of a material may having a low durometer such as in the range of 5-50 Shore A (ASTM D785). In some embodiments, it may have gripping features such as bumps, dots, mounds, grooves, or a surface texture (not shown). FIGS. 6A-6C illustrate an embodiment wherein the grip 27 comprises a segment of the handle 23, but one skilled in the art would realize that the operator may grasp the device 13 anywhere along the handle 23. Furthermore, some or all of the handle 23 may be overmolded, such that some or all of the handle 23 has a soft, flexible, grip-like texture and feel.

The handle 23 may, for example, be made of a metal such as steel, aluminum, titanium, or tungsten, or plastic, such as ABS, poly(methyl methacrylate) (PMMA), PEEK, Nylon, polypropylene, polyethylene, or polycarbonate. The handle 23 may be one-piece and rigid, it may be one-piece and flexible, or as illustrated in FIGS. 6A-6C, it may have a hinge 29. For example, in the present embodiment, the hinge 29 is an elastic or living hinge that allows the handle 23 to articulate in the superior-inferior direction. It is within the scope of this disclosure that the hinge 29 may be a living hinge or a mechanical hinge such as a pin joint, revolute joint, or ball and socket joint or any other articulable joint that allows the handle 23 to be articulated somewhere along its length. Additionally or alternatively, the hinge 29 may articulate in the lateral direction. The handle 23 may also be an entirely flexible member, for example, made of a flexible material such as silicone, rubber, or TPE, such that it may continuously flex throughout its length and be attached to the corneal shield 15 or to a stem 25 emanating therefrom. That is, the handle 23 may be an elastic tail or strap that emanates from the corneal shield 15 as long as it can transmit the forces from the operator's hand to permit control of the shield 15.

In embodiments, the handle 23, appendage 31, grip 27, stem 25, and shield 15 may be made of polymeric materials which may be made using any suitable manufacturing method such as 3-D printing, injection molding, reaction injection molding (RIM), or machining. Furthermore, by way of nonlimiting example, the polymeric materials may have a flexural modulus in the range of about 0.5 GPa to about 10 GPa (ASTM D790) or up to 19 GPa, for example, for materials that may have a glass or carbon fill.

FIG. 6B is a top view of the ocular protection device 13 of FIG. 6A. This view illustrates that the corneal shield 15 may by unsymmetrical in a lateral direction, across the eye. That is, there may be a tear-drop shape and/or longer section at the nasal end 37 as compared to the temporal end 39 to accommodate the asymmetry of the anatomy. Alternatively, the corneal shield 15 may be symmetrical in this direction.

The corneal shield 15 may come in a variety of sizes so that it may cover a variety of eye shapes and sizes; the width of the shield in the top view of FIG. 6B may be from about 15 mm-28 mm (nasal end 37 to temporal end 39). The corneal shield 15 has a smooth leading edge 21 that may be full-round, that is, the rounded edge diameter may be the same as the thickness of the shield 15. The edge should be smooth enough to be atraumatic to the eyelid, eye, and surrounding tissue. The shield 15 may be approximately 0.5 mm to 1.5 mm thick or up to 3 mm thick in some embodiments. The handle 23 may be centered on the corneal shield 15 where the stem 25 meets the shield 15, or it may be offset, as depicted in the present embodiment. Furthermore, the handle 23 may be offset on the shield 15 in the vertical (superior-inferior) direction.

A side sectional view of the device of FIG. 6B is shown in FIG. 6C to illustrate how the various components may be arranged. As illustrated, the corneal shield 15 has an eyelid surface 17 (proximal surface) and a corneal side 19 (eye-contacting, or distal side), and it may have a vaulted section at or near its apex 38, such that this region has a smaller radius of curvature than the more distal region of the shield 15. The vault enables the corneal shield 15 to provide clearance over the cornea (not shown) such that the outer sections of the shield contact the sclera predominantly. The corneal shield 15 has a smooth eyelid surface 17 and corneal surface 19, each of which may, for example, meet the standard of SPI-A3 (Society of the Plastics Industry) for surface finish. The corneal shield 15 may be vapor polished to achieve a smooth surface finish.

The corneal shield 15 of this and other embodiments disclosed herein may be made of plastic, elastomer, or metal depending on the procedure that is being conducted on the eyelids: examples of materials include metals such as steel, titanium, or tungsten, or a plastics, such as ABS, (PMMA), polyetherether ketones (PEEK), Nylon, polypropylene, polyethylene, or polycarbonate. For intense pulsed light (IPL) procedures, an opaque plastic, or a plastic with a coating that can effectively shield the eye from the light in the spectrum associated with Rosacea and MGD treatments is appropriate as is a metal corneal shield. IPL devices may, for example, produce light in the spectrum of approximately 500 nm to 1200 nm in wavelength. Additionally, the corneal shield 15 may have a coating (e.g., a chromophore) to help block light or laser transmission. For RF procedures, the corneal shield 15 may be electrically and thermally insulating so as to not transmit electrical or thermal energy to the eye, thus confining the energy to the eyelids. The thermal conductivity of the shield 15 may be less than about 1 W/mK and the electrical resistivity may be greater than about 1000 Ωm. For laser procedures, a metal shield made of, for example, steel or tungsten, may be used or a plastic corneal shield capable of blocking the laser, or a plastic corneal shield with a laser blocking coating may be used to attenuate the laser energy before it reaches the eye.

The stem 25 may be formed integral to the corneal shield 15, as shown in FIG. 6C, or it may be attached to the corneal shield 15 by a mechanical or chemical means, for example via a bonded connection or a mechanical snap fit (not shown). In the present embodiment, the stem 25 extends into the grip 27 wherein the two components are joined together by a press fit (interference fit) wherein the grip 27 may be undersized, compared to the stem 25, so that a press fit can be realized when the grip 27 is placed over the stem 25. Alternatively, the grip 27 may be overmolded onto the stem 25 and/or the appendage 31. The distance between the shield 15 and the grip 27 may be about 10 mm or any distance that allows the operator to fully treat up to the lid margin, while allowing room for the operator's hand to manipulate the handle, without obstructing the view of the area under treatment. Alternatively, the grip 27 may extend up to the corneal shield 15 as long as the thickness of the stem 25 and the grip 27 combined is small enough (about 2 mm or less than about 4 mm) to allow the eyelids to substantially close so that a treatment electrode can cover up to the eyelid margin without being blocked by any part of the ocular protective device 13. Likewise, the distance between the shield 15 and the hinge 29 may be about 20 mm or any distance that allows the handle 23 to be articulated so that the operator may fully access the lid margin in the vicinity of the stem while allowing room for a treatment handpiece and the operator's hand without obstructing the view of the area under treatment.

The appendage 31 may also be joined to the grip 27 by a press-fit or overmold, as illustrated above. The stem 25 and the appendage 31 may butt against each other or leave a gap 28 which serves as a natural hinge due to the reduction in stiffness from the gap between the two parts inside of the grip 27. The grip 27 may be thinned, necked-down, or scalloped 30 at the hinge 29 to tailor the stiffness of the hinge 29, as shown in FIG. 6C. Alternatively, the grip 27 may be overmolded with the stem 25 and appendage 31, thus joining them without leaving a gap between their ends. The appendage 31 may be oriented superior-inferior as shown in the figures, or it may be horizontal depending on the ergonomics of the underlying procedure and the treatment apparatus used. Furthermore, it is within the scope of this disclosure that the appendage 31 may have any shape that allows it to be manipulated by the operator; such shapes include but are not limited to: a bulge or enlarged portion, round, oval, solid, flat, spoon-like, cylindrical, a loop, or straight and elongate like a toothbrush handle. Embodiments disclosed herein, such as the present ocular protection device 13, may be provided sterile to the operator or may be sterilized in the clinic (e.g., autoclaved). Furthermore, the device 13 may be a single-use or multi-use device or a combination of single-use and multi-use (an example being a disposable, single-use, corneal shield 21 used in conjunction with an appendage 31, grip 27 or entire handle 23 that may be reusable). The device 13 may be sterilized by any medical device sterilization method compatible with the chosen material(s). Sterilization options include gamma radiation, ethylene oxide gas, steam autoclaving, or electron beam irradiation.

As conveyed in the cross-section shown in FIG. 6C, one skilled in the art would recognize that the components may be pressed together by the operator or a medical assistant/practitioner in the clinic. For example, the entire handle 23 (or only the appendage 31 and grip 27 together) may be provided as a standalone device that is reusable, while the corneal shield 15 may be a disposable element that is attached by the operator. The corneal shield 15 may have a stem 25 attached thereto, or a clip-in feature, to accept the grip 27 or appendage 31 and the corneal shield 15 may be a separate component allowing the ocular protection device 13 to be assembled in the clinic before a procedure. Or vice versa, the corneal shield 15 may be a reusable product that may be sterilized in the clinic while the appendage 31 and grip 27 may be a single-use or multi-use disposable. Various sizes of shields 15 may engage with the same handle 23, grip 27, or appendage 31 apparatus. Furthermore, the appendage 31 and grip 27 may not need to be sterilized, thus allowing the operator to use multiple sterilized corneal shields 21 with a single handle 23.

In embodiments where the corneal shield 15 is removable, the gap 28 may be adjustable by the operator to tailor the stiffness of the hinge 29. For example, the operator may pull the stem 25 distally so that it slides out of the grip 27 a distance to make the gap 28 larger, thus increasing the flexibility of the hinge 29.

In other aspects, the device 13 may have a safety-releasable joint. For example, if the patient perceives pain, he or she may suddenly pull away from the corneal shield, which is being held by the operator, putting undesirable pressure on the lids (and potentially rupturing the canthal tendons normally securing the lids in place). The risk of injury may be reduced if the grip 27 can be disengaged from the stem 25 with a force that is less than the force that may injure the patient. Additionally or alternatively, the appendage 31 and/or grip 27 may be able to breakaway from the grip 27. The breakaway force can be tuned to the desired force level by adjusting the amount of interference between the grip 27 and the stem 25 or appendage 31.

Figure 7:
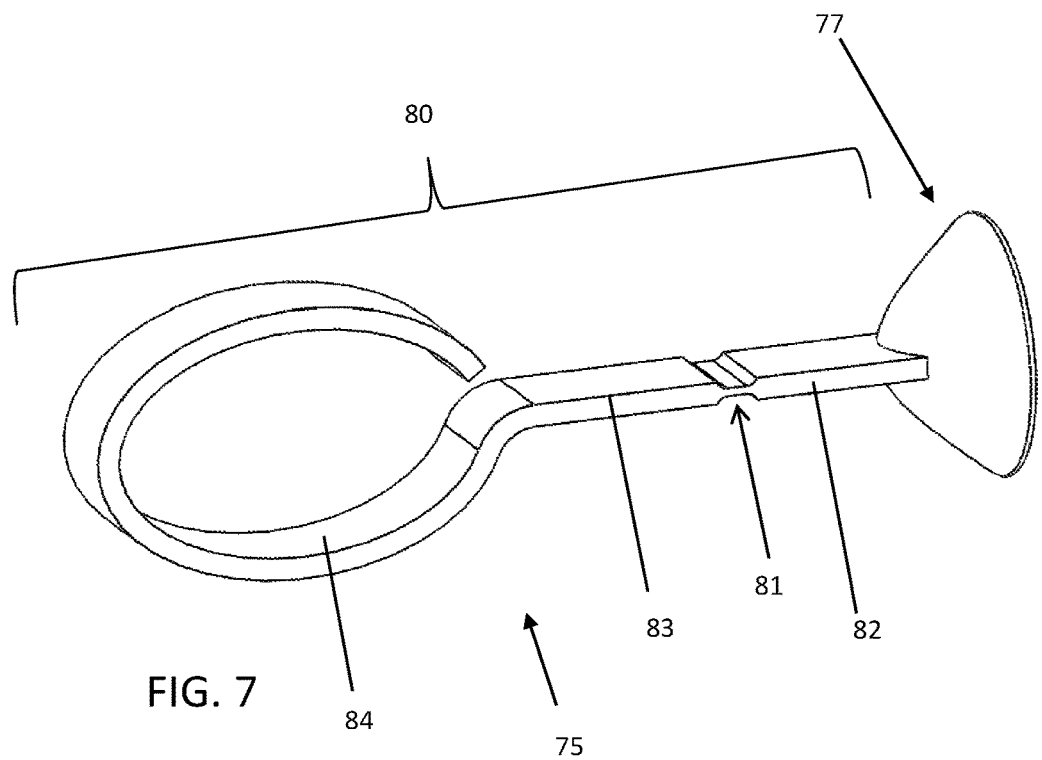
FIG. 7 is a perspective view of another embodiment of an ocular protection device.

In certain embodiments, the ocular protection device may be a single part (e.g., injection molded or 3D printed) as illustrated by the ocular protection device 75 shown in FIG. 7. A corneal shield 77 is attached to a handle 80 which may be entirely rigid, or it may have a living hinge 81 along its length as shown. The living hinge 81 may be spaced apart from the corneal shield 77 by a stem 82 that is rigidly attached to the shield 77. The length of the stem 82 may be enough to allow an operator to manipulate the stem 82 and the proximal handle 83 to put forces and moments on the shield 77 to protect the eye from the force caused by a treatment handpiece. As such, the stem 82 may be long enough (at least about 15-30 mm) for a finger to be placed on it without interfering with the treatment handpiece. The handle 80 may have a loop 84 or other feature at its proximal end to facilitate manipulating the device 75. The ocular protection device 75 may be low in cost as it may be a single-use disposable, or it may be reusable. Grip features, texture, words, or other features may be molded into the plastic or otherwise labeled onto the material. The ocular protection device 75 may composed of any suitable plastic material such as those mentioned in other embodiments herein or other materials suitable for use as a living hinge such as Nylon, polypropylene or polyethylene. Furthermore, all or part of the handle 80 may be overmolded with a softer polymer, such as an elastomer, TPE, silicone, or rubber to provide grip or aesthetic features. The corneal shield 77 may have a harder or stiffer material than the handle, as such, the ocular protection device 75 may be comprised of multiple materials, for example, the corneal shield 77 may be made of ABS plastic while the handle 80 may be made of polypropylene; the two materials may be co-molded or joined together by any method for joining plastics such as bonding, ultrasonic welding, solvent bonding, or heat staking/thermal bonding, or there may be a snap fit or hinge joining the two components.

Figure 8A:
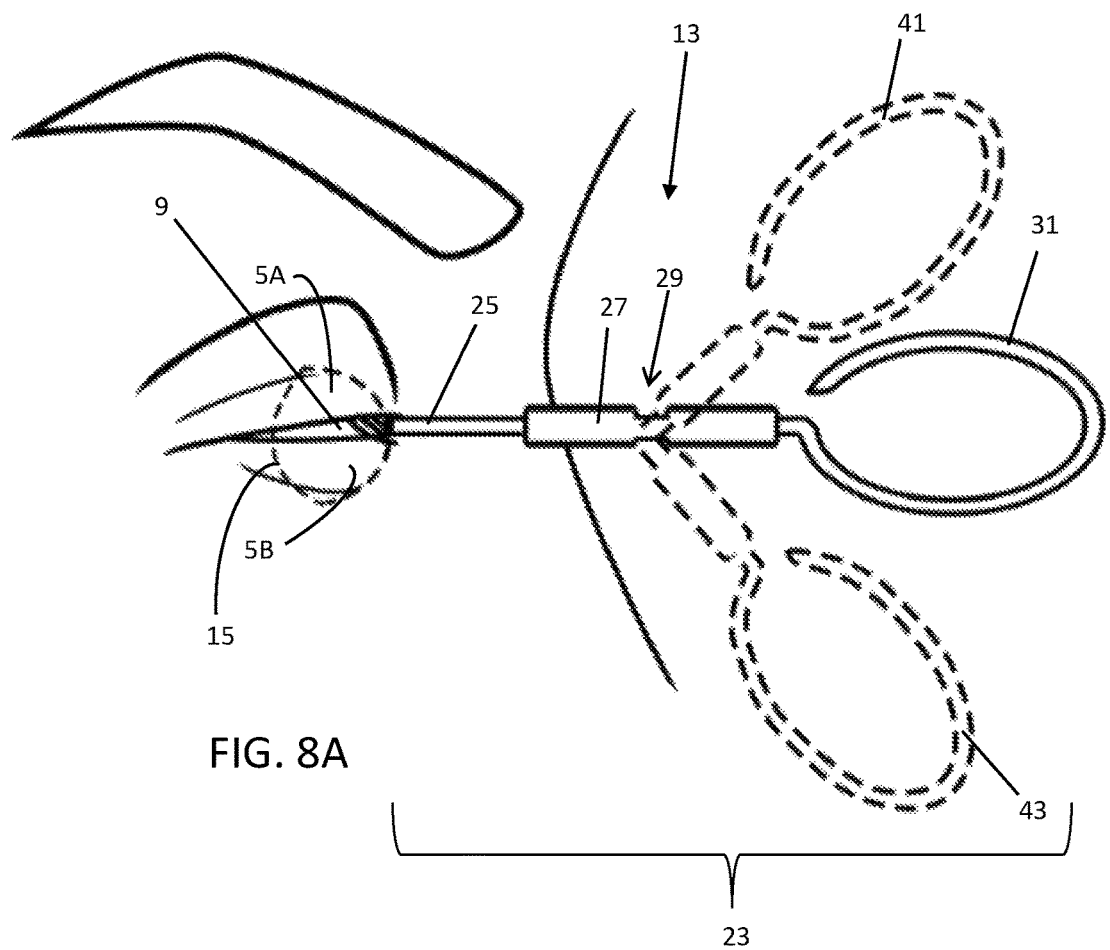
FIG. 8A is a side view of an ocular protection device with a hinge, shown articulating into three different positions.

FIGS. 8A-8E show the ocular protection device 13 from FIGS. 6A-6C in several exemplar scenarios of use. With reference to FIG. 8A, dotted line images show a profile view of the right eye area with the appendage 31 in the up position 41 and the down position 43 in relation to the neutral axis (unflexed) position. When articulated in the up position 41, the operator has a clear view of the lower eyelid 5B for treatment or visualization. Furthermore, a thermal imaging device will have a more direct line of sight to the lower eyelid 5B because the appendage 31 and the operator's hand (not shown) will not block the view. Likewise, the down position 43 affords the operator and an imaging device a more clear view of the upper eyelid 5A.

Figure 8B:
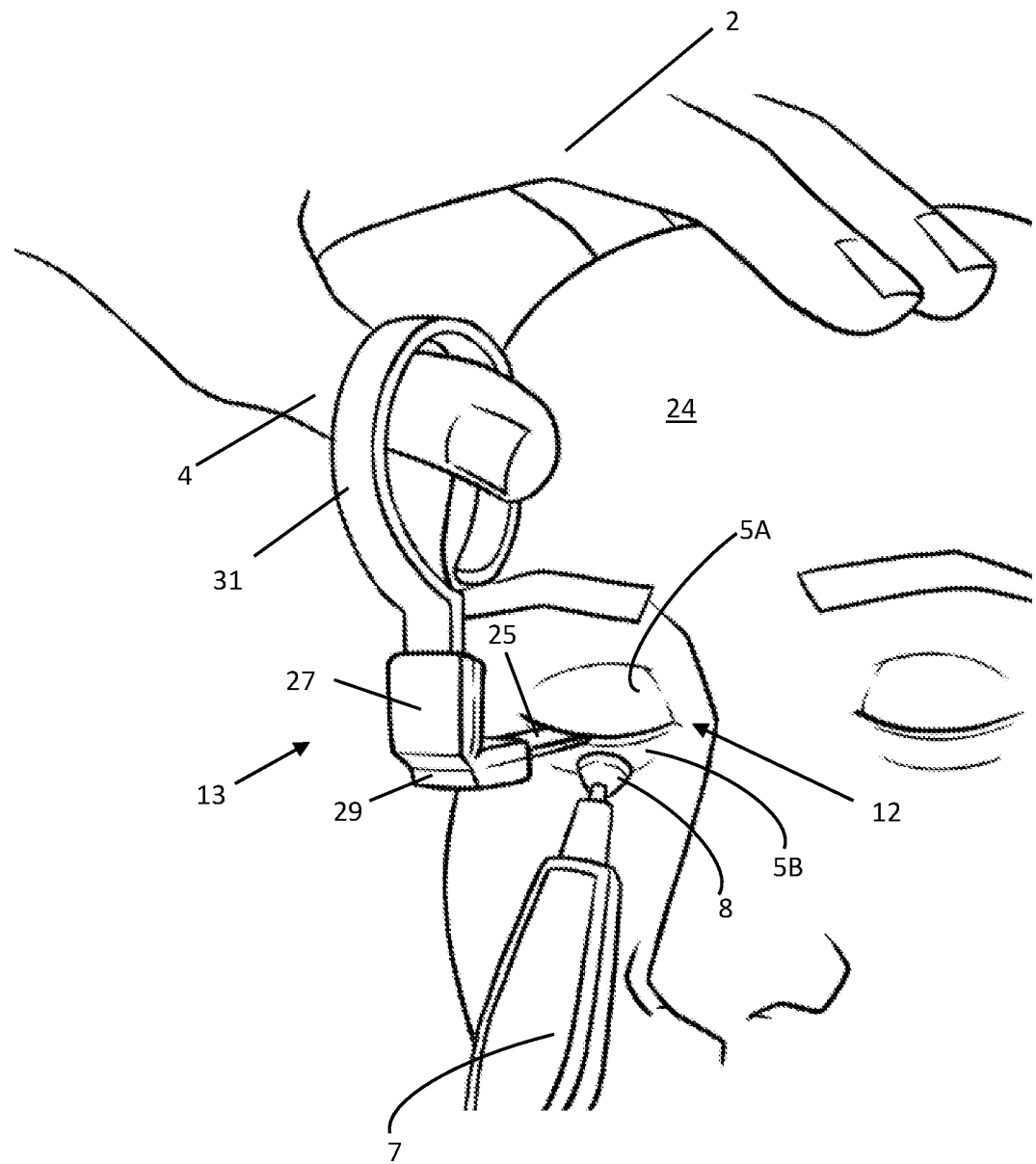
FIGS. 8B-8E are perspective views of an operator using the ocular protection device of FIG. 8A using various hand positions.

The ocular protection device 13 provides the operator with many ways to grasp the device 13 while the operator adjusts the position of the corneal shield 15 or provides back pressure (counterforce or tension) on the eyelids (5A and 5B) to react forces the from the handpiece 7. FIG. 8B shows one such scenario in which the operator is treating the lower eyelid 5B with a handpiece 7 while using the ocular protection device 13 as it is articulated in the upward position, or superior to the lid margin 12. The device 13 may pivot beyond 90 degrees, or until it touches the patient's head 24 for stability; additionally or alternatively, the operator's protection hand 2 may contact the patient's head 24 to stabilize the device 13 while the operator treats the lower eyelid 5B. In this arrangement, the operator's thumb 4 may pull upward on the appendage 31 thus creating a reaction force on the lower lid to counteract the pressure from the tip 8 of the handpiece 7. The hinge 29 may have a mechanical hard stop (not shown) such that it does not articulate beyond a certain angle, allowing the operator to apply torque to the corneal shield 15 (not shown) when forcing the appendage 31 against the hard stop.

Figure 8C:
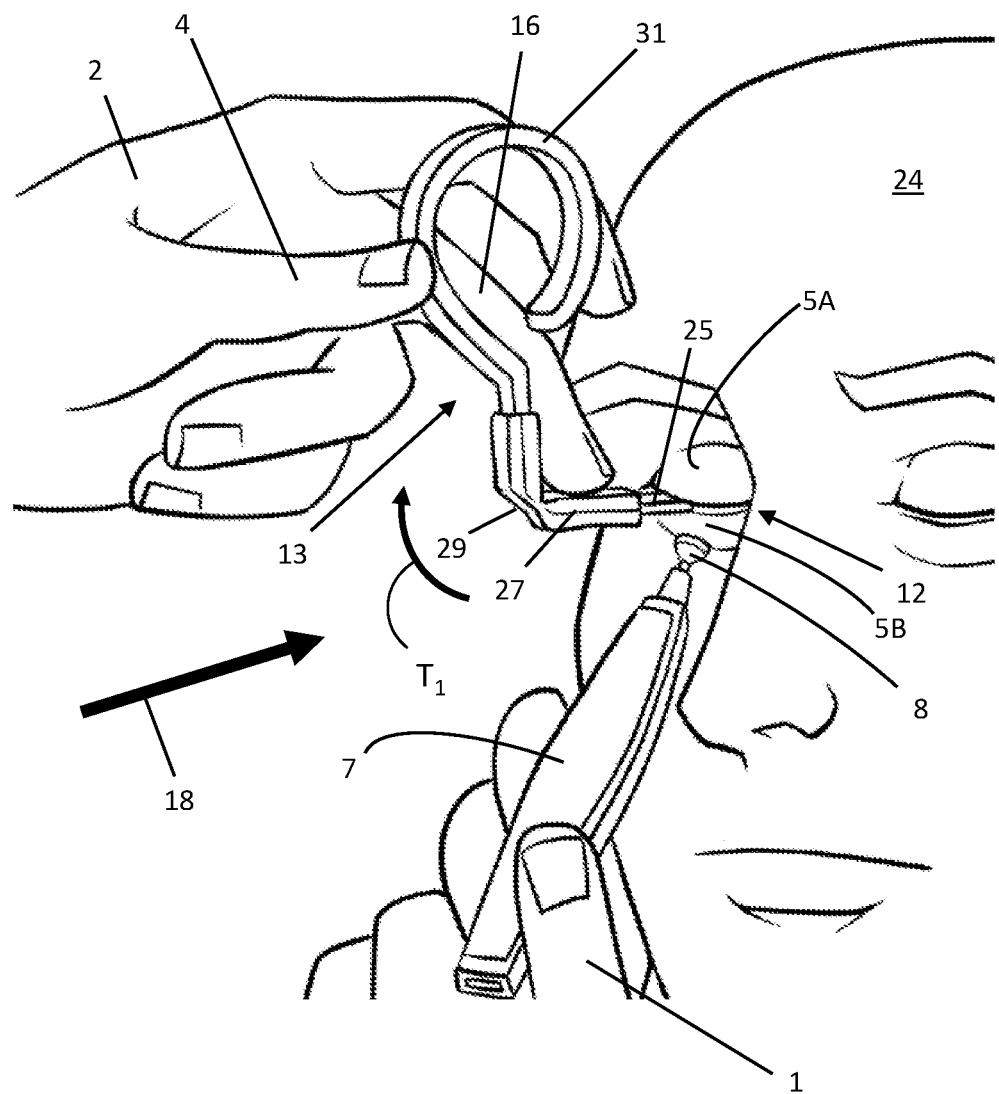

FIG. 8C shows the device 13 manipulated in another manner. The operator's protection hand 2 is shown holding the appendage 31 while pressing down on the stem 25 and grip 27 with his or her middle finger 16. The net effect of this is to create a torque Ti (see arrow) that may be transmitted to the corneal shield because the stem 25 is rigidly connected to the shield. This torque Ti provides an opposing force at the shield to counteract the force of the tip 8 of the handpiece 7 as it compresses the lower eyelid 5B. i.e., the torque action may pull proximally on the corneal shield 15 (under the eyelids) without translating the corneal shield 15 upward, which would put an unwanted force on the upper eyelid 5A, at the lid margin 12. Additionally or alternatively, the operator may press his middle finger 16 against the appendage 31 in this configuration to put tension on the entire corneal shield 15, thereby directly creating a counterforce for reacting the force on the lower eyelid 5B due to the tip 8.

As further illustrated in FIG. 8C, the tip 8 of the handpiece 7 is bearing on the lower eyelid 5B at a location that is not aligned with the center of the ocular protection device 13, or stem 25. This may arise while the lid is being treated because the handpiece 7 is moved around the lower eyelid 5B dynamically. To fully balance the force input from the handpiece 7, the operator's middle finger 16, as it bears down on the grip 27, can put a lateral force (toward the nose) on the shield to counteract the off-center force applied by the tip 8 of the handpiece 7.

The device 13 allows the operator or a visualization system, such as an IR camera, to view the lower eyelid 5B while it is being treated as illustrated in FIG. 8C. The line of sight 18 (arrow) illustrates that the device 13 and the operator's protection hand 2 may be moved out of the line of sight 18 when the ocular protection device 13 is articulated. The length from the corneal shield (under the eyelids 5A and 5B) to the hinge 29 is notable in that a very short length may limit the different ways that the operator can handle and manipulate the ocular protection device 13. Furthermore, if the length of the stem 25 is zero, such that the device 13 hinges at or near the corneal shield 15, then the operator will be unable to apply a moment to react the force of the handpiece 7 on the eyelid 5B because the shield 15 will rotate about the hinge and transmit the force to the eye. In general, the orientation and articulation angle of the ocular protection device 13 depends on the requirements of the treatment being conducted at any given moment; multiple optional configurations in which the operator may grasp and manipulate the ocular protection device 13 provides the operator with many options to suit his or her treatment style.

Figure 8D:
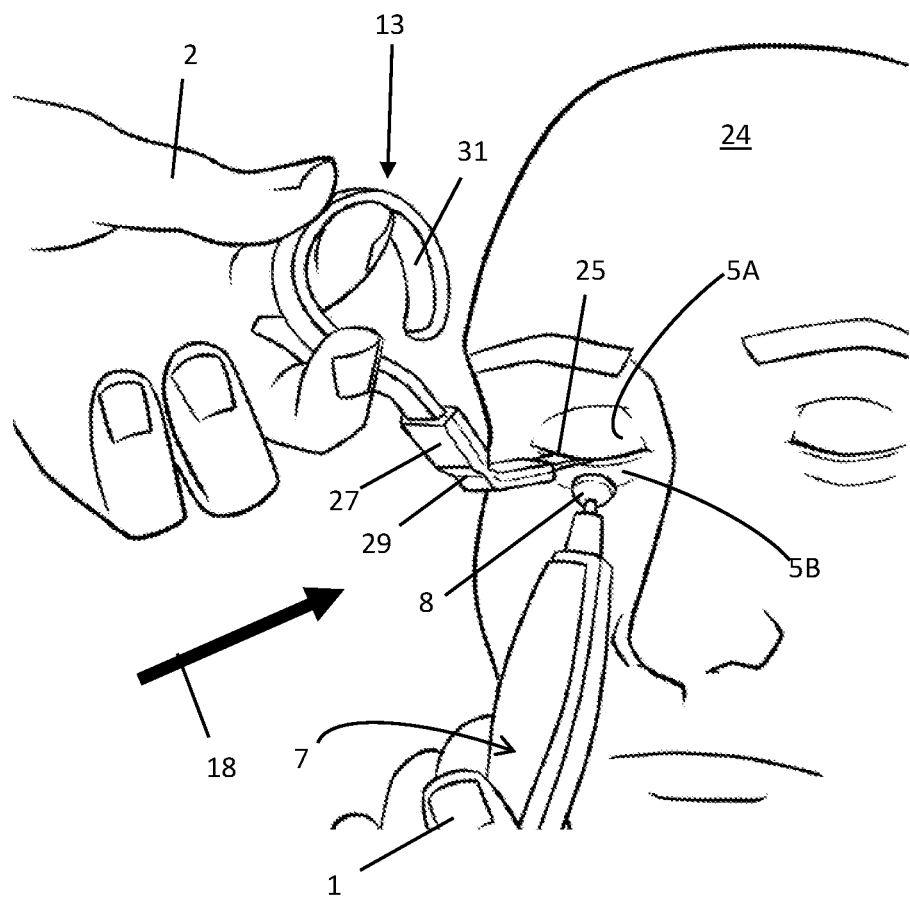
Figure 8E:
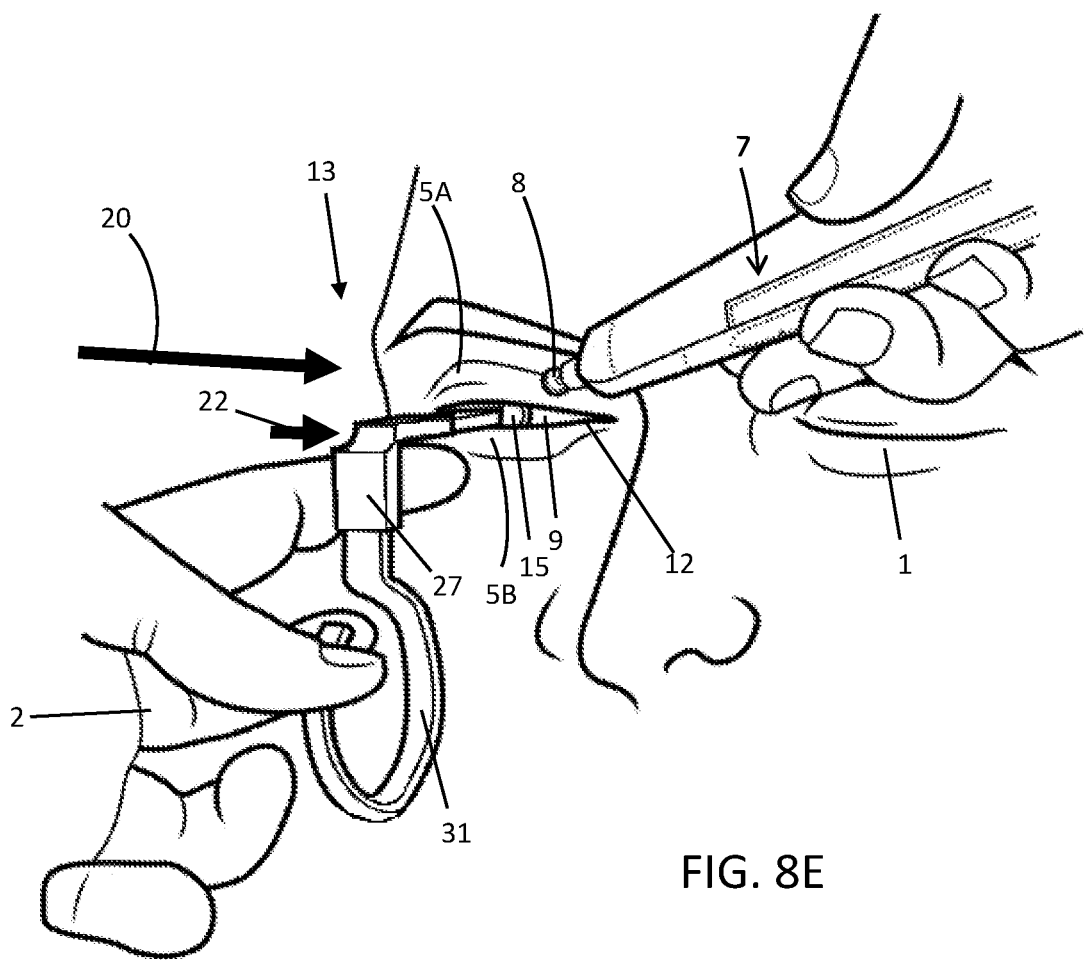

Several more non-limiting example embodiments of an ocular protection device are shown in FIGS. 8D-8E. In FIG. 8D the operator's protection hand 2 is shown manipulating the device 13 while the hinge 29 is open at an oblique angle; the operator is pulling proximally and superiorly to pull the shield against the lower eyelid 5B to counteract the force from the tip 8 of the handpiece 7. This arrangement also leaves the field of view open as shown by the line of sight 18 and the relatively high position of the operator's protection hand 2.

The upper eyelid 5A may be treated in a similar manner as the lower eyelid 5B, as shown in FIG. 8E. The ocular protection device 13 may be articulated such that the appendage 31 is in the downward, or inferior direction, with respect to the eye 9. This allows the line of sight 20 to the upper eyelid 5A to be preserved while allowing the operator to manipulate the corneal shield 15 as desired. In the treatment scenario shown in FIG. 8E, the eyelids 5A and 5B, are slightly open showing part of the corneal shield 15 as it resides on the eye 9 to more particularly illustrate the action of the operator while treating the eye when the corneal shield 15 is misaligned with respect to the top 8 of the handpiece 7. Assuming that the operator's treatment hand 1 has placed the tip 8 of the handpiece 7 onto the eyelid as shown, the operator's protection hand 2 may guide the ocular protection device 13 laterally toward the nose (indicated by arrow 22) so as to move the corneal shield 15 underneath the location to be treated by the tip 8, thus protecting the eye 9 and surrounding tissues. In practice, the operator may do this by feel, if he or she cannot see the corneal shield 15, or by seeing the edge of the corneal shield 15 through the lid margin and noticing that it does not overlap with the tip 8 of the handpiece 7.

Figure 9A:
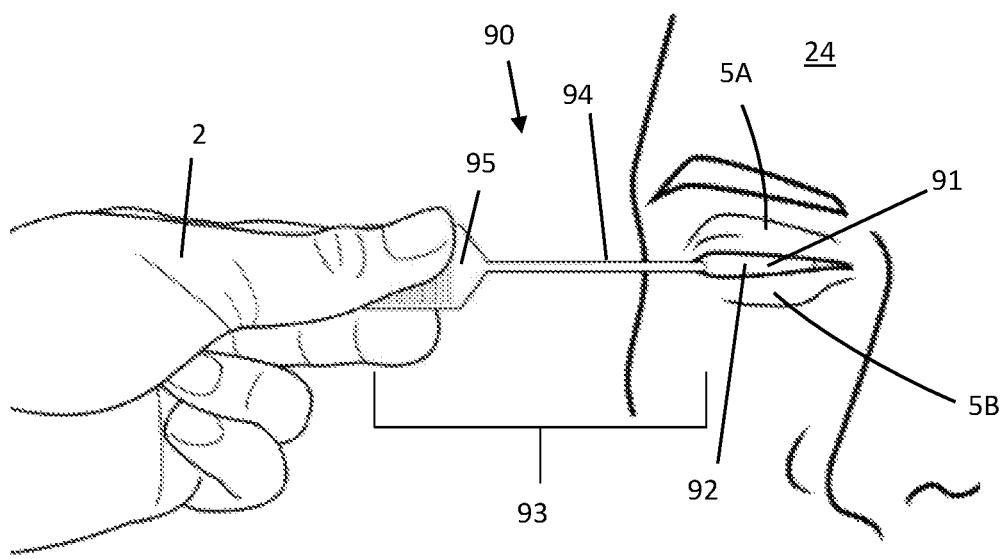
FIG. 9A is a perspective view of another embodiment of an ocular protection device having a handle disposed to a side of the corneal shield, the shield shown inserted in a patient's right eye.
Figure 9B:
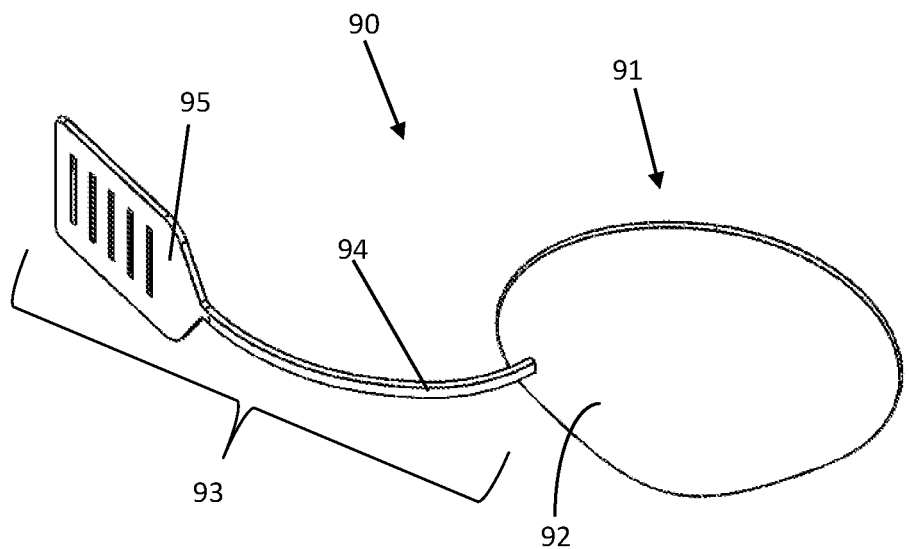
FIGS. 9B and 9C are different perspective views of the ocular protection device of FIG. 9A FIGS. 10A and 10B are views of another embodiment of an ocular protection device having temperature sensors.
Figure 9C:
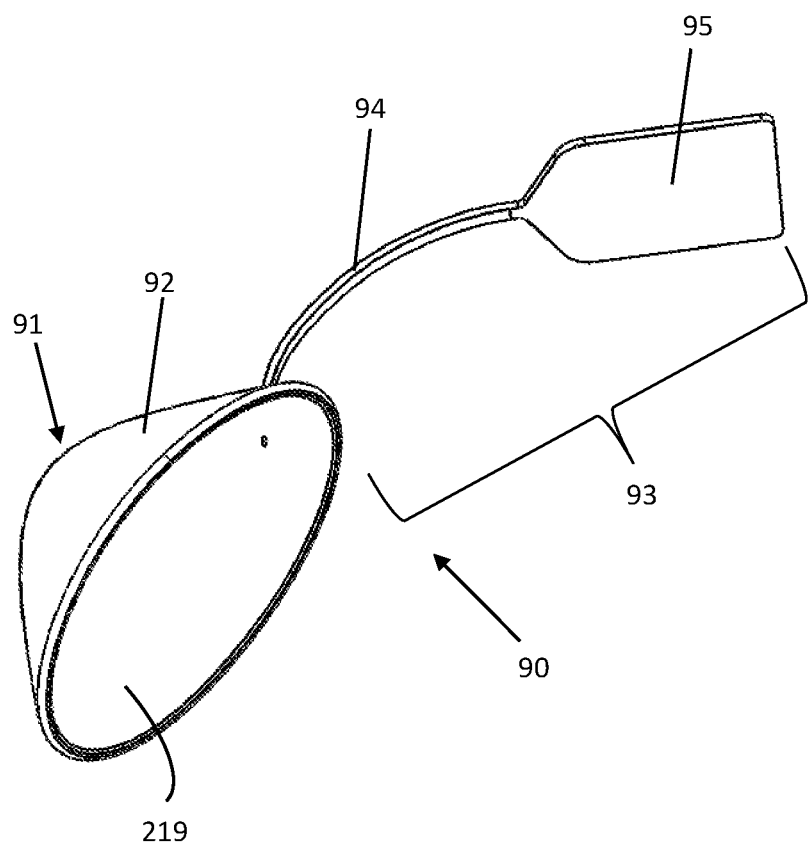

FIGS. 9A-9C illustrate yet another embodiment of an ocular protection device 90. For context, the ocular protection device 90 is initially shown installed under the eyelids 5A and 5B in FIG. 9A. The device 90 comprises a corneal shield 91, having an eyelid side 92 and a handle 93 rigidly attached thereon. The handle 93 includes a stem 94, which may be attached near an end (temporal or nasal) of a corneal shield 91, and an appendage 95 located at a proximal end of the stem 94; the handle 93 may be rigid or stiff enough to control the position of the corneal shield 91 while an eyelid 5A (or 5B) is being treated. As in the other embodiments disclosed, the eyelids 5A and 5B close onto the stem 94 during use, as such the stem may be small in height or less than about 4 mm thick. The length of the stem 94 may be long enough to span laterally beside the eyelid 5A or even beyond the patient's temple so that the operator may grasp the appendage 95 and/or stem 94 such that the operator's hand is beside the patient's face, leaving the space in front of the eyelids 5A and 5B unobstructed. If the appendage 95 resides close to the temple or forehead, the operator's hand may rest his or her hand on these areas of the patient's head 24 for stability while holding or articulating the appendage 95 or handle 93. The device 90 may also be oriented in the opposite direction so that the handle 93 extends over or beyond the nose, similarly allowing the operator's hand to be out of the way while controlling the corneal shield 91.

Similar to other embodiments disclosed herein, the device 90 may be made of a one-piece molded plastic, or it may be a multiple piece assembly, for example the corneal shield 91 may be a separate part that may be attached during manufacturing or in the clinic. The device may be overmolded entirely, or selectively, to create grip features, different colors, or texture. Furthermore, the device 90, or only the corneal shield 91, may be made of a metal in order to be compatible with certain eye treatment procedures. Examples of candidate materials for the ocular protection device 90 include metals such as steel, titanium, or tungsten, or a plastics, such as ABS, acrylic (PMMA), PEEK, Nylon, polypropylene, polyethylene, or polycarbonate.

The ocular protection device 90, works in a similar fashion to the aforementioned embodiments illustrated herein, in that it allows the operator to manipulate the corneal shield 91 by handling the stem 94 and/or the appendage 95. For example, if the stem 94 is relatively rigid, the operator can manipulate the corneal shield 91 directly, that is he or she can move the corneal shield 91 around the eye without directly handling the corneal shield 91. The operator may also react the force of the treatment device (not shown) by putting torques and/or forces on the appendage 95, stem 94, or both simultaneously to protect the eye. With the operator's hand outside of the line of sight of both eyelids 5A and 5B, they can be treated simultaneously or in close sequence without having to reposition the device 90; furthermore, a thermal visualization system can image both eyelids at the same time to quickly assess the temperature.

FIGS. 9B and 9C show this embodiment on two opposite sides via perspective views. The handle 93 in this example may have a stem 94 and an appendage 95, but there may also be a hinge (not shown). The stem 94 may be approximately 10-40 mm in length and curved (as shown) or straight to provide clearance so that the operator's hand is out of the way, allowing the eyelids to be treated and visualized. This length of the handle 93 may be patient specific, such that the length of the stem 94 or appendage 95 may vary in various product sizes. The length of the handle may be about 25 mm to 100 mm. Likewise, in this and other embodiments, the corneal shield 91 may be offered in several sizes to accommodate various eye sizes and shapes. For example, a "medium" corneal shield may be approximately 26 mm across its major diameter, while a size "small" may be 3 mm-5 mm shorter and a size "large" may be about 3 mm-5 mm longer. Likewise, a "medium" corneal shield may be approximately 24 mm across its minor diameter while a size "small" may be about 3 mm-5 mm shorter and a size "large" may be about 2 mm-5 mm larger across the minor diameter.

The stem 94 should be stiff such that it will not deform appreciably while being used to manipulate or control the corneal shield 91. In some embodiments, the stem 94 may be made of a malleable material, such as an easily bendable metal, such as annealed 304 stainless steel, which may be coated with a nonconductive material (e.g., an elastomeric overmold) to insulate the metal from electrified treatment devices. The malleable material can be set to a desired shape by the operator so that the stem 94 and appendage 95 are in a desired configuration and the shape may be adjusted multiple times during treatment.

As illustrated in the disclosed figures and descriptions, there are multiple ways to manipulate the embodiments of ocular protection devices to create tension on the eyelids, to move the corneal shield, and to cause a reaction force (counterforce) against a handpiece. As the method embodiments disclosed herein are manual procedures, the operator senses feedback as he or she treats the lid with one hand while handling the ocular protection device with the other hand. The figures demonstrate by way of non-limiting examples that the various embodiments allow for a variety of orientations and grip arrangements to suit the treatment modality so that the operator can effectively shield the eye from the forces imposed by the handpiece. It has been observed in clinical practice that the operator adjusts hand position intuitively because he or she feels, through the ocular protection device, the forces that he or she is applying with the handpiece onto the corneal shield. While sensing these forces, the operator continually manipulates the ocular protection device to counteract the force applied, to move the corneal shield, and to move his or her hand from obstructing the view of the eyelids. In addition, the operator may feel the built-up waxy blockages as he or she massages the eyelid. That is, holding the handpiece and ocular protection device while massaging the eyelid may provide feedback as to the texture, lumps, and undulations of the waxy substance in the glands; when this material melts, the operator feels the higher, firm, wax melt and flatten especially as he or she approaches the lid margin. In some embodiments, the ocular protection device may have force sensors built into the handle, stem, or corneal shield to provide feedback to the operator regarding the force applied to the eyelid by the handpiece or an expressor used for expression. The force sensors may be strain gages, for example, or pressure sensors on the surface of the corneal shield or the stem.

Figure 10A:
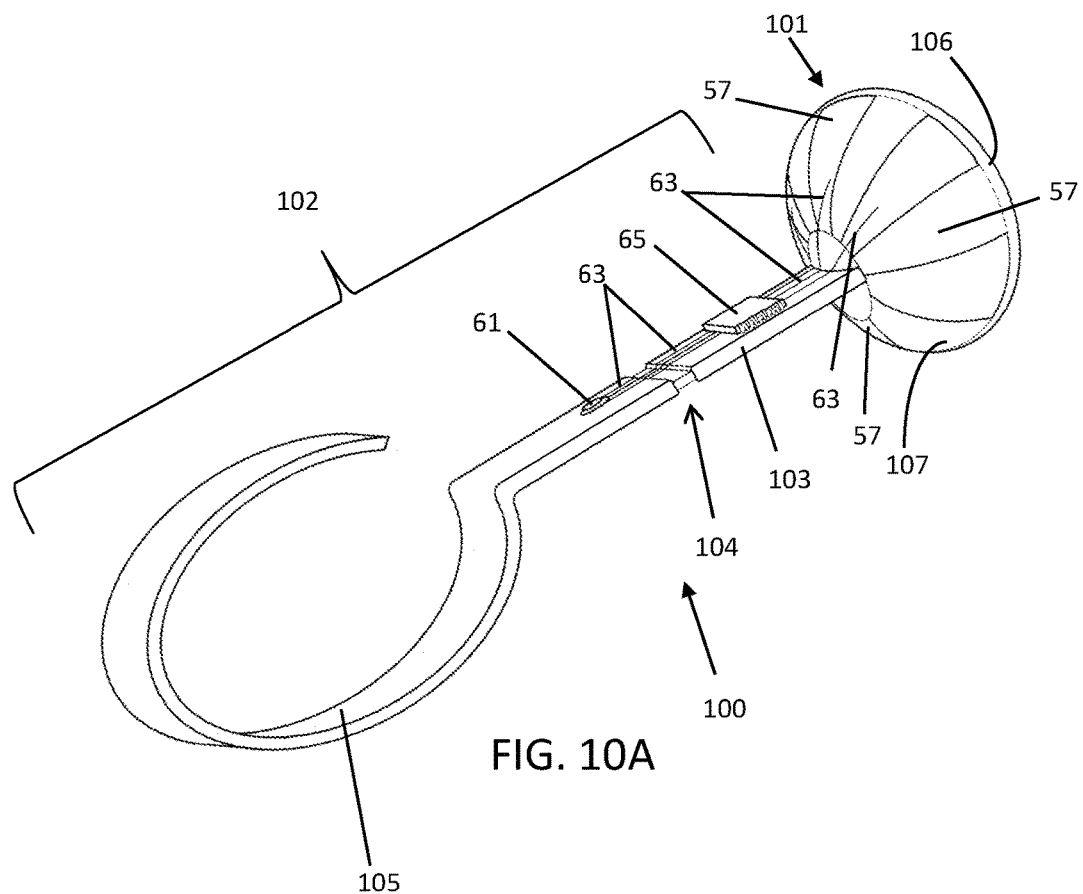
Figure 10B:
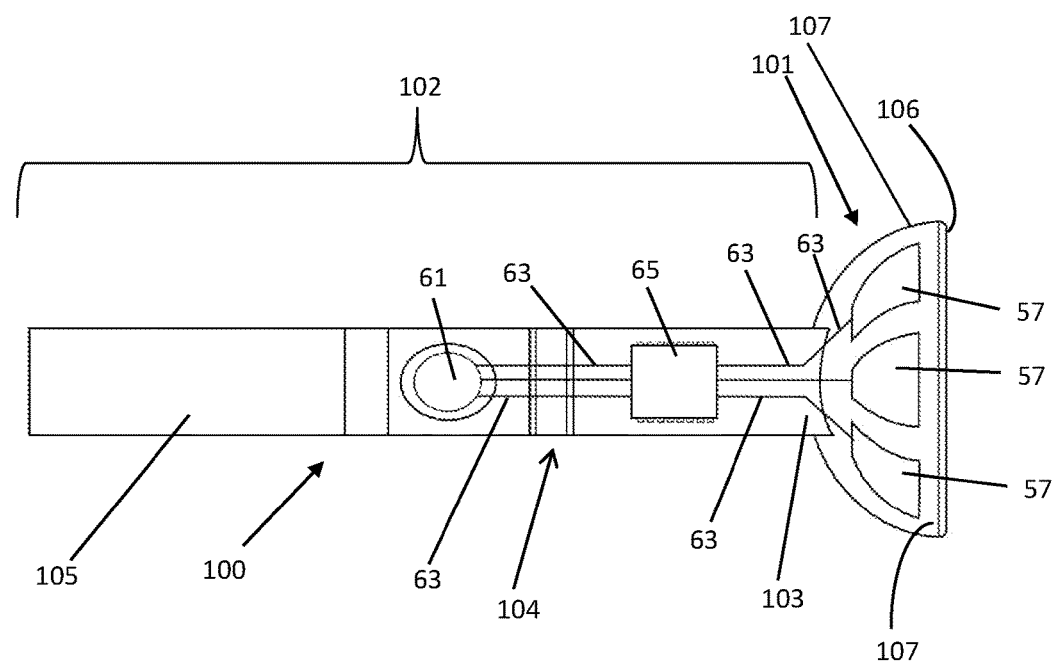

Some embodiments may also have temperature sensing integrated into the ocular protection device; FIGS. 10A-10B show such an embodiment. This ocular protection device 100 may be similar to the ocular protection device embodiments described herein in that it may have a corneal shield 101 and a handle 102 extending therefrom. Optionally, a hinge 104 may be located on the handle 102 between the corneal shield 101 and the appendage 105. The ocular protection device 100 may comprise one or more temperature sensors 57 located on the eyelid side 107 of the corneal shield 101. The sensors may extend from the intersection of the shield 101 and stem 103 up to the edge 106 of the shield 101 to substantially cover the inside of the eyelid. The one or more sensors 57 may be capable of producing a single, average, temperature of the eyelid, or they may be able to map a temperature distribution across the eyelid. Alternatively, they may map to segments of the eyelid enabling a discrete number of temperature measurements across the eyelid. Additionally or alternatively, there may be multiple sensors across the eyelid (not shown) oriented along a horizontal direction along the eyelid.

The temperature sensors 57 may be connected to digital or analog electrical circuitry on the ocular protection device 100 or remote from the device 100. For example, the device 100 may include one or more processors 65 on-board having the capability of receiving an electrical signal corresponding to temperature and converting it into an output that may be perceived by the user or transmitted via wired or wireless connection to another device such as, but not limited to, a smartphone, tablet, personal computer, remote server, or laptop computer. The ocular protection device 100 may also have an onboard battery 61 to power the processor 65, sensors 57, and any other visual display or signal transduction means configured to facilitate an output that the operator may perceive. The battery 61 may be replaceable, single-use, or rechargeable as the ocular protection device may have charging circuitry and a charging port. The processor 65 or other onboard device may manage the power between a battery 61 and other electrical elements in the system. The sensors 57 and components may be connected through various electronic connections 63 (e.g., wires or flex circuit) that may be embedded in or attached to the device 100. As mentioned above, the ocular protection device may be tethered by a cable such that some or all of the functionality described above, except for the temperature sensing, is processed remotely.

The temperature sensors 57 disclosed herein may be of any type as long as they fit under the eyelid without causing undue discomfort. Examples include, but are not limited to: thermistors, resistance temperature detector (RTD), thermocouples, or integrated silicon temperature sensors such as in a MEMS temperature sensor that may have integrated electronics. Corneal shield materials used in the present embodiments may include thermally sensitive indicators such as dyes, which provide information as to temperature due to the change in color.

Figure 11:
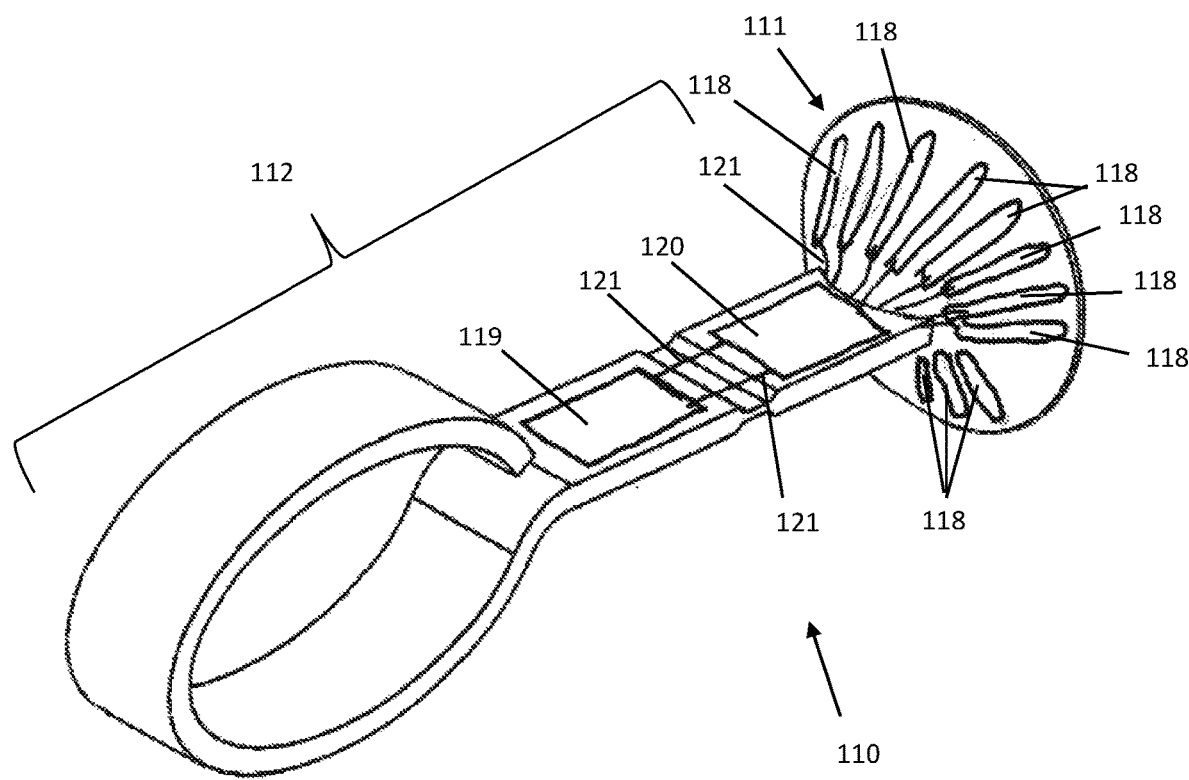
FIG. 11 is a perspective view of another embodiment of an ocular protection device having temperature sensors.

A higher resolution sensor array is illustrated in another embodiment shown in FIG. 11. The ocular protective shield 110 has a multitude of temperature sensors 118 on the eyelid surface 117 of the corneal shield 111 offering more spacial resolution in the temperature mapping of the eyelid. Embodiments may include hardware and software for communicating the temperature to the user located on the handle 112; the present embodiment has a user interface 119 in communication with a processor 120 connected through various electronic connections 121 (e.g., wires or flex circuit). The user interface may be a display (e.g., LED or LCD) that portrays an image or number(s) corresponding to an average temperature or the temperature distribution on the inside of the eyelid as sensed by the temperature sensors 118, or it may be one or more LEDs or light elements that emit light corresponding to temperature; for example, an array of LEDs wherein each LED lights up according to the temperature of the corresponding temperature sensor 118 on the corneal shield 111. The LED's may be a linear array or groups of linear arrays that light up in a bar-chart fashion— each bar indicating the temperature of a given region of the corneal shield 111. Alternatively, there may be a single LED or light element that lights up when the eyelid is at the desired temperature, for example, the temperature being averaged across the eyelid. The LED's (not shown) may be located on the handle 112 or may be on the corneal shield 111 such that they illuminate through the eyelid to indicate the local temperature where they illuminate. For example, each temperature sensor 118 may have an LED that lights up when a certain temperature is achieved. Alternatively, each sensor 118 may have an array of, for example, three sensors of different colors wherein each color corresponds to a different temperature. Thus, the different sensors 118 may each have one or more corresponding LED's that light up when a desired temperature, that may be set by the operator, is reached. This may inform the operator as to the temperature of various segments of the eyelid so that he or she may adjust the heating or expression pattern accordingly. Additionally or alternatively, the user interface 119 may be a sound generator such as a speaker (e.g., a piezoelectric element) that creates a sound when the desired temperature is reached or a series of different sounds corresponding to the temperature.

Various embodiments of a method or technique and instrumentation to treat eyelids with an energy source while protecting the eye will now be disclosed. The procedures may be performed with any energy source that is intended to heat the eyelids from either the outside or inside of the eyelid, for example for treating diseases such as MGD (the example presented herein) or for aesthetic treatments. The order of steps described herein is for illustrative purposes only and is not intended to limit the scope of the invention, as various alternative combinations or permutations of the sequence of steps are contemplated.

Before commencing treatment, the operator may asepticize the lids using an aseptic cleanser such as Avenova® and saturated Qtips® by wiping over the lid margins. Alternatively, the patient may receive a mechanical debridement and/or BlephEx® treatment to clean and prepare the lid margins. The eye may be anesthetized with a numbing agent such as a drop of Proparacaine™. A corneal shield inserted by, for example, having the patient "look down" while the corneal shield is inserted under the upper eyelid, then as they "look up" pulling the lower lid down until the shield is set into place on the eye. An ocular protection device may be used such as illustrated in embodiments described in this application which are suitable for holding and manipulating the corneal shield; see, for example, FIGS. 8B-8E, which show an operator treating an eye using an exemplar ocular protection device 13 and handpiece 7. For certain procedures, such as RF treatment, a gel is applied over the eyelids. The lids may be treated consecutively or simultaneously depending on the type of treatment device used.

The following exemplar treatment method pertains to the use of a contact-based device with a tip which heats the eyelids via RF or thermal conduction to the eyelid. If the operator starts with the upper eyelid, he or she may use a gripping material such as a 4×4 gauze to get some traction on the brow to stretch the upper eyelid into a smooth, tight transition so that the tip 8 of the handpiece 7 slides and has access to the lid margin with a stable corneal shield positioned over the cornea.

In order to raise the temperature of the eyelid, the operator turns the handpiece 7 on and moves the tip 8 back and forth in lateral rows over the tarsal area (and slightly broader areas, and may give direct contact with the lash/lid margin). As the goal in this phase is to heat the eyelid, any massaging motion that substantially covers the surface area of the eyelid may be used to bring the eyelid up to temperature. Examples include successive lateral (temple to nose) rows with each row higher or lower than the previous one, successive vertical columns up and downward while moving the column strokes across the eye, zigzag patterns, random motions, or circular massage motions. Note that the ocular protection device 13 may be handled by the operator throughout the procedure to move the corneal shield 15 to protect the area being treated and/or to provide back pressure against the tip 8 of the handpiece 7 to protect the eye 9. In embodiments, the ocular protection device 13 may have a handle 23 that is hinged or otherwise movable to allow the operator to move his/her protection hand 2 out of the view and clear of the handpiece 7 as illustrated above.

Clinical experience has shown that some patients may experience pain if the eyelid temperature increases too quickly, so multiple passes with the handpiece may be necessary to raise the temperature gradually. This iterative approach may be conducted in what is termed treatment segments or "passes" using one of the many patterns that may be used to heat the eyelids to bring them to the desired temperature as illustrated above. One may conduct several initial passes to heat the eye, then conduct several more treatment passes wherein the glands are expressed. One skilled in the art would realize that there are many combinations and permutations of heating and expressing and these are contemplated as being within the scope of this application. Likewise, there are different types of devices that may be used to heat the eyelids, for example, the handpiece may have one or more plates in contact with one or both eyelids transmitting energy via heat conduction or RF; the plates may substantially cover the entire eyelid surface so that minimal movement is applied. Additionally or alternatively, other modalities may be used to transmit energy to the eyelids such as intense pulsed light (IPL), convective heat transfer, laser, ultrasonic (vibrational) energy, or microwave energy while some modalities may not require contact with the eyelids. Examples of commercial devices include the TempSure™ and Pelleve™ Wrinkle Reduction Systems, ICON™ and Lumenis M22™ Universal IPL machines, the Almirall THERMIsmooth™ device, and the MIBO Thermoflow™. These devices and methods, as well as any others capable of heating the eyelids to a temperature that allows obstructions in the Meibomian glands melt, loosen, or soften, are contemplated by this disclosure.

Figure 12:
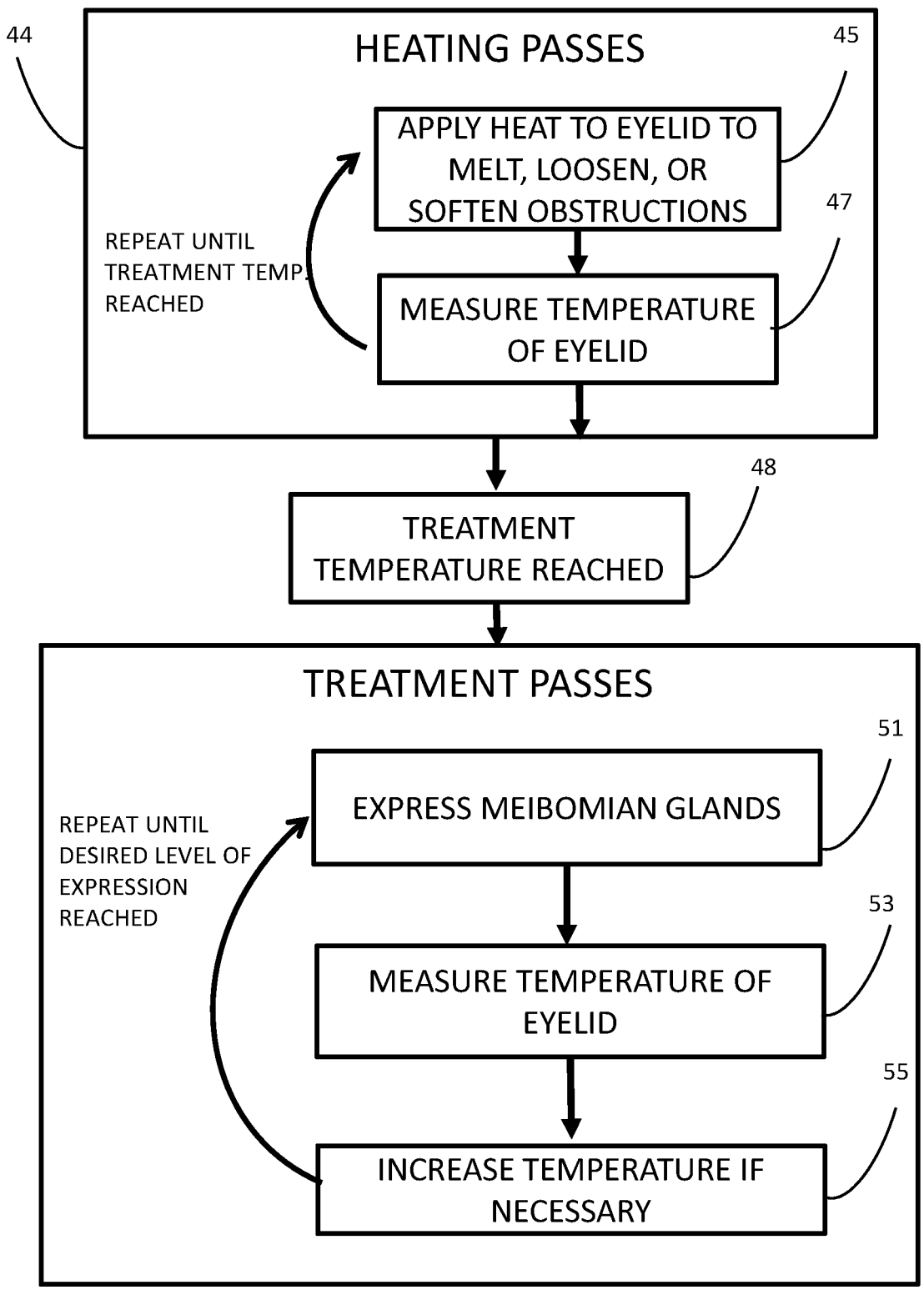
FIG. 12 is a flowchart illustrating an exemplar method for treating Meibomian gland disease.

FIG. 12 is a flowchart representing an exemplar method of treating eyelids. On the heating passes (steps 45 and 47) the operator applies heat while measuring temperature, aiming for a temperature that may be below the therapeutic range; for example, 38 degrees Celsius. The heating passes (steps 45 and 47) are continued for a period of time (approximately 20 seconds) until the temperature of the lid reaches the first desired temperature increase. During this first pass, the temperature may be measured multiple times or continuously with any device for measuring the temperature of the eyelid. On the second pass, the procedure is repeated until a new target temperature is met, which may be 40° C. for example. Consecutive passes are repeated until the eyelid temperature reaches a treatment value (step 48) which may be 42° C. (or, for example, 43-50° C.) or that which is clinically appropriate for the patient being treated. There may be one or more heating passes 44 indicated in FIG. 12 depending on the patient, the operator's technique, and the energy used, and the operator may check the temperature incrementally to avoid overheating the eyelid, that is, unless automatic temperature feedback control is used to control the amount of energy automatically as further described below.

Next, the operator expresses, or milks, the waxy substance from the Meibomian glands (MG) by massaging the lids with slightly overlapping massaging expressions in the direction of the Meibomian glands (step 51). For example, the operator may conduct numerous (e.g., 10) top-to-bottom (upper eyelid) or bottom-to-top (lower lid) strokes moving from one side of the lid to the other, and then repeating MG expression on the lid in the same manner again. This expression stage may be conducted with a lid expression device made of metal or plastic which may have a lip or edge for applying a discrete line of pressure to the eyelid which can be drawn on the lid toward the lid margin to exude the waxy material from the glands. Additionally or alternatively, the lid expression may be accomplished by dragging the tip 8 of the handpiece 7 (FIGS. 8B-8E) toward the lid margin; the handpiece may be either on or off during this phase of treatment. Other examples of lid expression embodiments are described below. Each expression step may last approximately 20 seconds or less.

During expression, the operator may reduce the pressure on the cornea or even lift the eyelid slightly off of the cornea, using the handle 23 of the ocular protection device 13 (FIGS. 8A-8E for example) and carry out the expressions over the eyelid (e.g., only moderate pressure of approximately 6-10 PSI may be applied). Bending/flexing the ocular protection device 13 at the hinge 29 allows the operator to place his hand clear of the tip 8 of the handpiece 7 to work over the lid while also enabling him/her to view the eyelid. The same method and apparatus (e.g., handpiece 7, and ocular protection device 13) can be used to treat both eyes. Multiple treatment passes may be conducted in order to achieve the desired level of Meibomian gland expression. The temperature of the lid may be measured (step 53) and increased (step 55) during these treatment passes by reapplying energy if the temperature falls below the target treatment temperature. In practice, approximately three expressions (step 51) may be conducted to treat an eyelid.

The present embodiments are not limited to any particular approach to measuring the temperature of the eyelids, and one of skill in the art will recognize that there are many types of sensors capable of reading the lid temperature, such as for example, sensors located on the corneal shield as previously described herein and shown in FIGS. 10A, 10B, and 11. Alternatively, temperature sensing may be integrated into the tip 8 of the handpiece 7 (refer to FIG. 3). For example, the tip 8 may include a temperature sensor such as a thermocouple or thermistor so that the temperature may be measured when the tip 8 is in contact with the eyelid 5A. Additionally or alternatively, thermal radiation sensor(s) may be used to measure the eyelid temperature via the energy radiated from the lid. Examples include non-contact methods such as one or more spot IR sensors or an IR imaging system (e.g., FLIR™) that reads the thermal radiation of the entire eyelid at once. In the latter scenario, the operator may have an assistant point the IR camera at the eyelid during treatment, or the IR camera may be mounted on a fixed or movable arm so that it is aimed at the patient's eyelid. The operator may then view the image on the IR camera or another monitor or computer during the procedure.

In other embodiments, one or more sensors may be attached to, or integrated into, the treatment handpiece. Thus, the operator may monitor temperature while he/she is heating or expressing on the eyelids, or the operator may aim the sensors at the eyelid to determine the temperature at a desired location on the lids; in some embodiments this may be accomplished with the handpiece in contact with the eyelids, or it may be held away from the eyelids while measuring temperature, depending on the type and configuration of the sensor. Additionally or alternatively, any type of contact-based temperature measurement methods may be employed such as thermistors placed in contact with the eyelid or integrated within the corneal shield to read the temperature of the inside of the eyelid.

Now with reference to FIGS. 13A-13E, which illustrate treatment handpiece embodiments having one or more integrated or attached temperature sensors. By way of nonlimiting example, the sensor embodiments disclosed herein may be any sensor capable of measuring the temperature of the eyelid such as IR sensors or fiber optic sensors; the latter may be configured to contact the surface of the skin or to read the temperature from a distance. The signal from the sensor(s) may be electronically processed on the handpiece or processed on a remote terminal, controller, or computer that may be connected to the handpiece via cables or a wireless connection. A temperature display may be located on the handpiece or located separately from the handpiece being remotely connected to a computer or control terminal. The temperature sensor(s) may be integral to the device or retrofitted onto a commercially available handpiece.

Figure 13A:
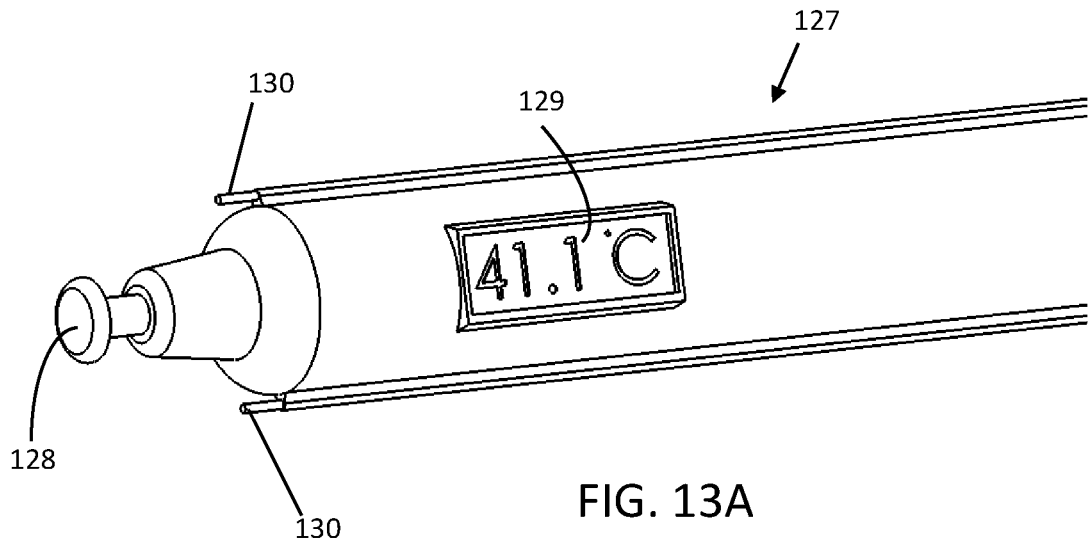
FIGS. 13A-13E illustrate various embodiments of a handpiece having onboard temperature sensors.
Figure 13B:
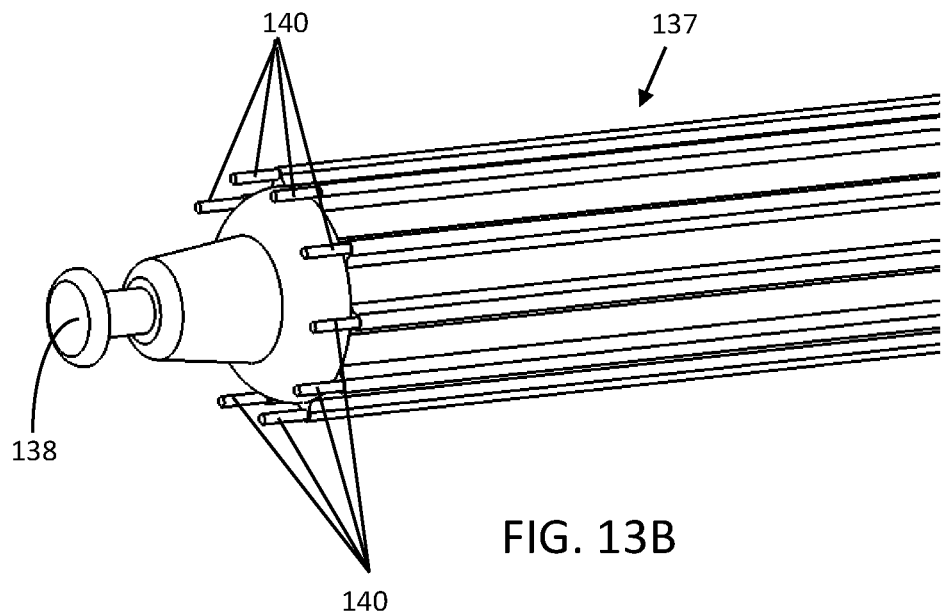
Figure 13C:
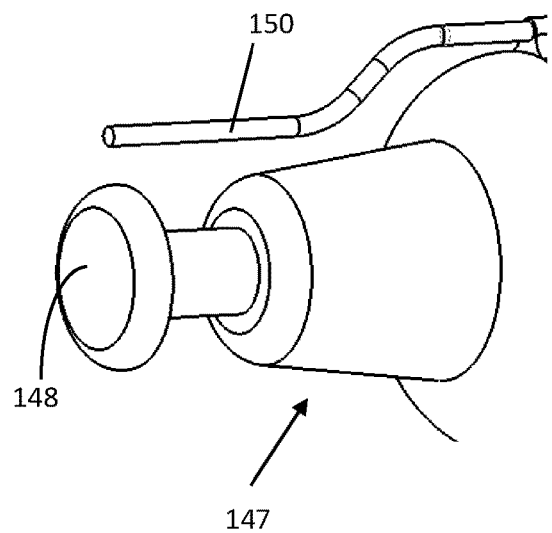

FIG. 13A shows an embodiment of a handpiece 127 with two temperature sensors 130 mounted on it. The ends of the sensors 130 are proximal to the tip 128 of the handpiece 127 such that they are capable of measuring the temperature of the eyelid from a distance. The handpiece 127 may include a temperature display 129 on the handpiece 127 that the operator may read during the procedure. A single temperature sensor may be used, or a plurality of sensors may be used, and the results individually displayed, averaged, or the lowest or highest temperature of the group may be displayed or recorded. FIG. 13B shows a handpiece 137 with temperature sensors 140 arranged in an array around the handpiece 137. The sensors 140 may be arranged diametrically close to the tip 138 to measure the temperature of the skin around the tip 138. In another embodiment, a temperature sensor 150 having a curve that allows it to be adjacent to the tip 148 of a handpiece 147 is shown in FIG. 13C. The sensor 150 may be proximal to the tip 148 or flush with the tip 148 to have contact with the skin. In FIGS. 13A-13C the sensors are shown located around the periphery of the handpiece, and they may be integrated into the handpiece or retrofitted in these or similar configurations.

Figure 13D:
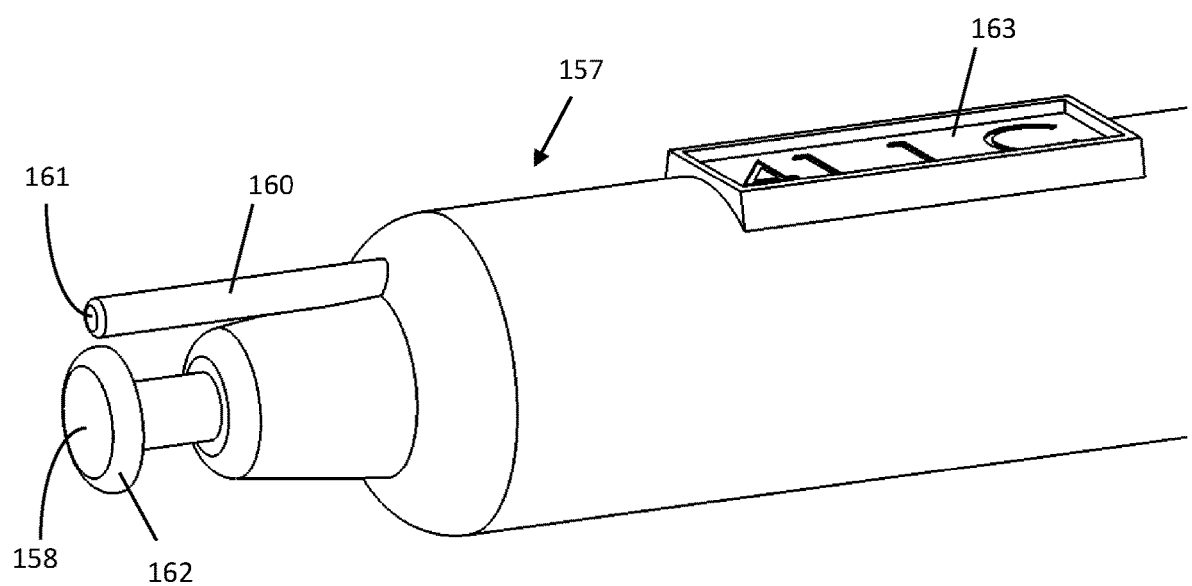
Figure 13E:
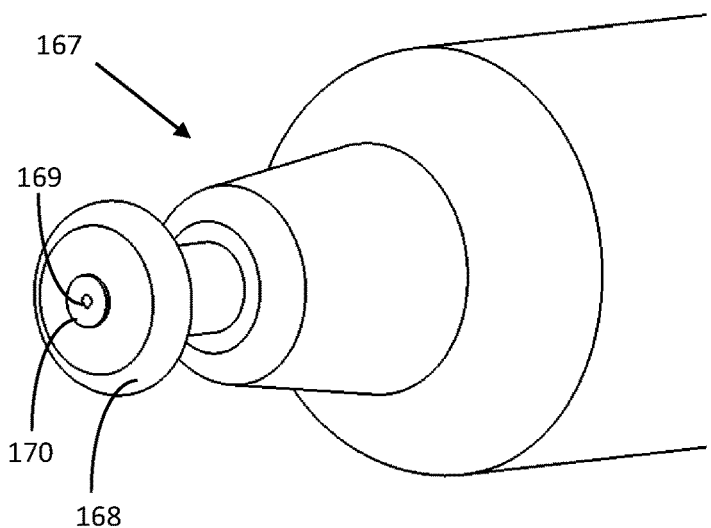

FIG. 13D illustrates an embodiment of a handpiece 157 having an integral temperature sensor 160 such that the sensor tip 161 is close to the edge 162 of the tip 158. The sensor tip 161 may be flush with the handpiece tip 158 or proximal thereto, and the handpiece 157 may have a temperature display 163. Another embodiment of a handpiece is shown in FIG. 13E. The handpiece 167 may have a temperature sensor 169 in the tip 168 that may read the temperature of the skin underneath the tip 168. The end of the sensor 169 may be flush with the tip 168 or proximal to the tip, and the sensor 169 may have an insulating material 170 around it to isolate it thermally and/or electrically from the tip 168. By way of nonlimiting example, the sensor 169 may be contact-based, using technologies such as RTD, thermistor, thermocouple, or fiber optics, or it may be a non-contact sensor such as a fiber optic or IR sensor.

In embodiments, whether the temperature sensors are on the handpiece or the ocular protection device, the system may have temperature feedback control. That is, temperature sensors located on the handpiece, the ocular protection device, or remote from the devices, may automatically sense temperature and provide a signal to the operator (visual, tactile, or audible) that a certain temperature threshold is reached in a certain area, prompting the operator to move to another location on the eyelid or to begin the expression process. The operator may set the temperature threshold manually. Additionally or alternatively, the feedback control system may directly control the temperature of the lid through an electronically controlled feedback loop in which the eyelid temperature is measured by the sensors, and this information is fed into a controller which controls the handpiece by, for example, adjusting the power supplied to the device.

Just as there are many different approaches to measuring temperature in accordance with the devices and methods disclosed herein, there are also many different approaches to the steps of expressing the Meibomian glands once they are melted, softened, or loosened, all of which are within the scope of this disclosure. For example, the operator may use his/her finger to purge the glands by stroking on the outside of the lid in the direction of the glands, or he/she may use forceps with paddle or plate-shaped tips to squeeze the lids. In order to increase the expression force while reducing the force on the eye, a rigid backing or support on the inside of the lid may be used. For the manual finger expression approach, the operator may use a cotton swab or similar device on the inside of the lid to purge individual glands or a set of glands.

The ocular protection devices disclosed herein may provide a firm backing surface to react the force of expression and to protect the eye as the operator may pull on the handle to add opposing pressure to the inside of the eyelid to react the force applied to the outside of the eyelid during expression. This serves to shield the eye from the force of expression, while increasing the pressure on the eyelid and the Meibomian glands, allowing a higher force to be applied because the force is reacted by a relatively hard surface, the corneal shield, compared to the eye.

As illustrated above (e.g., FIGS. 8A-8E), the tip 8 of the handpiece 7 may be used to express the glands. The tip 8 may have a conical or domed contact surface and a round shape with a diameter of about 8 mm, or between about 5-15 mm, for example. The tip 8 may have any shape that facilitates expression and heating while being able to fit onto the surface of the eyelid. That is, the treatment tip may have a contact face that is a fraction of the area of the eyelid, having a size of about 4 mm, or having a size approximately as long as the eyelid, or approximately 25 mm or more. As the size of the tip 8 approaches the dimensions of the eyelid, heating may involve minimal motion of the tip, or none at all; that is, it may be held substantially statically while heating the lids. Rather than using the contact face during expression, an edge of the tip may be used to localize the force to "scrape" the lid as further described below.

Figure 14A:
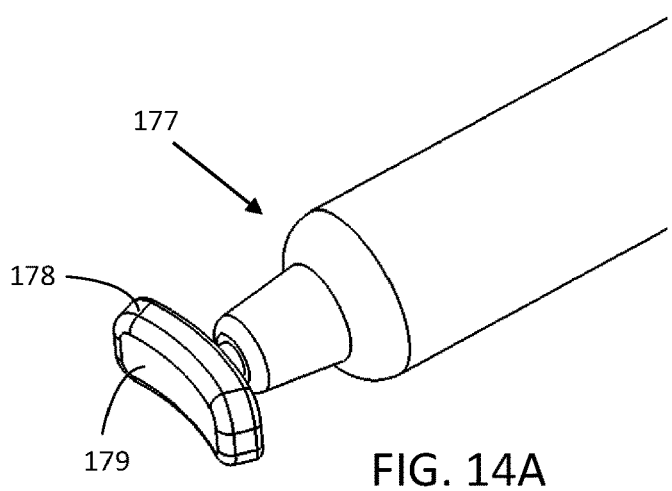
FIGS. 14A-14C show an embodiment of a handpiece with an oblong tip.
Figure 14B:
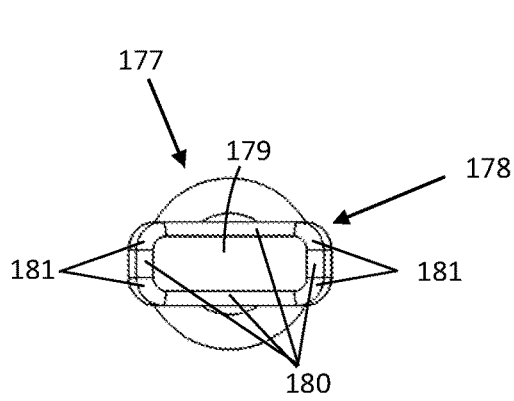
Figure 14C:
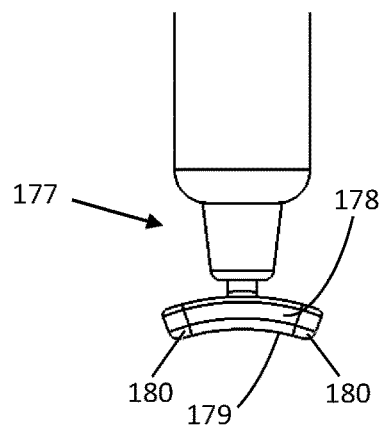

By way of nonlimiting example, FIG. 14A shows a perspective view of a handpiece 177 having a tip 178 with a concave face 179 and an oblong shape that is longer in width than in height as shown in the front view of FIG. 14B. The tip 178 may have rounded edges 180 and rounded corners 181 so that it may glide smoothly across the eyelid without pinching, catching or digging into the skin. FIG. 14C shows a top view illustrating the curvature of the concave face 179. The curvature may be similar to that of the eye, or approximately 12 mm in radius, or it may be slightly smaller, such as 10 mm or substantially larger, up to a flat surface or even slightly convex. As shown in FIG. 15, the tip may be unsymmetrical as illustrated in the front view of an embodiment of a tip 189 of a handpiece 187 for treating eyelids. The tip 189 has an upper edge 188 that may be curved so that it may conform to the shape of the eyelid. The handpiece 187 may be rotated over to be used on the adjacent eyelid. The lower edge 190 may be sharper than the upper edge 188 to facilitate expression, especially if the operator tilts the tip 189, while expressing, to predominantly use the lower edge 190.

In some embodiments, Meibomian gland expression may be performed by a separate device such as an expressor (e.g. a scraper, wiper, or squeegee-like device) the expressor 200 shown in FIG. 16A. The expressor 200 may have a handle 201, a shaft 205, and an expressor tip 202. The expressor tip 202 may be approximately 4 mm high and about 10 mm long or about 3 mm to 6 mm high and about 8 mm to 15 mm long, or as long as a typical eyelid margin (about 25 mm-30 mm). The front face 204 of the expressor tip 202, as shown in FIG. 16B may be straight, or curved as shown, and the cross-sectional shape may any shape such as a flat plate, round, or oval (ellipse) as shown in FIG. 16C. For expression, the operator may use the front face 204 or the edge 203 for increased pressure. The expressor tip 202 should be smooth and rounded on the corners to be atraumatic to the skin. In embodiments, the expressor tip 202 may be a rolling element (not shown), similar to a rolling pin, with a shaft and a rolling element to express and exude the glands as it is rolled along the eyelid toward the lid margin. The expressor tip embodiments may be made of any material appropriate for contact with the skin such as metals like stainless steel, or plastics such as ABS, Nylon, or PEEK. Plastics, or other materials that are substantially thermally insulating, will not transfer significant heat from the eyelid during expression. Expressor embodiments may be single-use or reusable and may be compatible with sterilization by, for example, electron beam, gamma radiation, steam autoclave, or ethylene oxide gas.

Figure 17A:
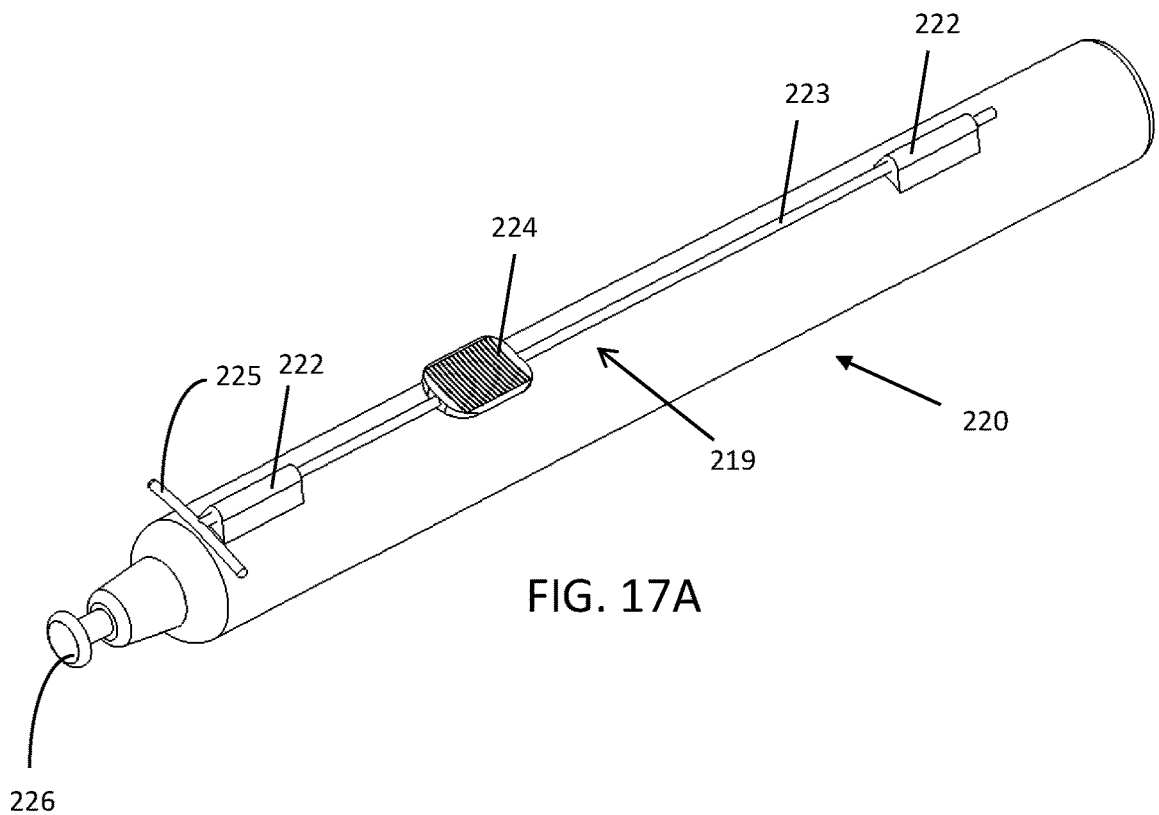
FIGS. 17A and 17B show an embodiment of a handpiece having an attached eyelid expressor.
Figure 17B:
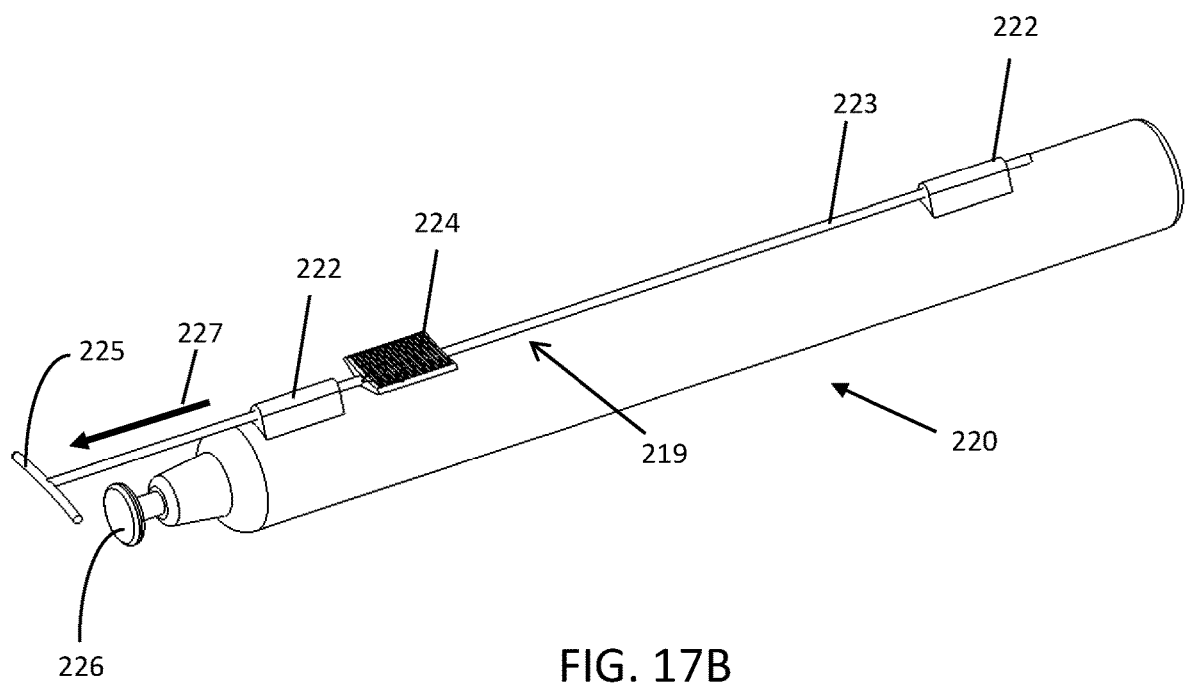

In embodiments, the expressor may be integrated into or otherwise attached to the treatment handpiece so that it may be conveniently accessed during the procedure. One skilled in the art will recognize that there are many ways to integrate an expressor with a handpiece and that it may be movably attached or detachable. For example, FIG. 17A shows an expressor 219 slideably attached to a treatment handpiece 220 such that its shaft 223 can translate along the handpiece 220 via one or more guides 222. The expressor 219 may have a tip 225 that is stowed out of the way during the heating phase, for example, while the handpiece tip 226 may be in contact with the lid (e.g., RF) or when the handpiece 220 heats from a distance (e.g., IPL). As illustrated in FIG. 17B, the user may advance the expressor 219 by pushing it via, for example, a finger grip 224 attached thereon such that the expressor tip 225 extends beyond the handpiece tip 226 as indicated by the arrow 227. The expressor tip 225 extends far enough that the handpiece tip 226 will not contact the patient while the operator performs expression; for example, the expressor tip 225 may extend greater than about 5 mm beyond the handpiece tip 226.

The expressor 219 may have one or more detents (not shown) allowing it to stay in place at various states, such as when it is fully extended and fully retracted. The expressor 219 may be removable from the handpiece 220 for cleaning or replacement. Furthermore, in some embodiments, the expressor 223 may be retrofitted to a handpiece 220 via straps or other attachments.

By way of nonlimiting example, other expressor embodiments using vibration or fluids may be used. For example, an expressor may vibrate at low frequencies in the 1-20,000 Hz range, or up to ultrasonic frequencies while expressing the glands. Alternatively, a jet or blade of forced air may be used to apply pressure to milk or express the glands, or a jet or blade of liquid may be used to apply a focused spot or line of pressure to the lid. The liquid may be encapsulated in a bladder to contain the fluid.

While the invention disclosed herein has been particularly shown and described with references to example embodiments thereof, it will be understood by those skilled in the art that various changes in form and details may be made therein without departing from the scope of the invention encompassed by the appended claims. While the above is a description of certain embodiments, various alternatives, modifications, and equivalents may be used. The various features of the embodiments disclosed herein may be combined or substituted with one another. That is, each of the components of the various embodiments may be combined with each other and that the components of one embodiment may be used with the components of another embodiment. Therefore, the above description should not be taken as limiting the scope of the invention which is defined by the appended claims.

What is claimed is:

1. An ocular protection device comprising:
   a corneal shield configured to fit underneath eyelids, the corneal shield having an inner surface configured to prevent damage to an eye;
   a handle rigidly connected to an outer surface of the corneal shield, the handle configured to protrude between closed eyelids; and
   wherein the handle includes a hinge that is offset from the corneal shield, and the handle is sufficiently long to allow an operator to control the corneal shield via the handle and wherein the hinge permits the operator to have an unobstructed view and access to the eyelids while maintaining control of the corneal shield.

2. The device of claim 1, wherein the handle has a length of at least about 25 mm.

3. The device of claim 1, wherein the handle and shield are integrally formed.

4. The device of claim 1, wherein the hinge is offset from the corneal shield by at least 15 mm.

5. The device of claim 1, wherein the hinge is a living hinge.

6. The device of claim 1, wherein the hinge comprises a junction piece that joins sections of the handle together.

7. The device of claim 6, wherein the hinge is a living hinge.

8. The device of claim 6, wherein the junction piece is an overmold that connects the handle sections.

9. The device of claim 1, wherein the shield is made of a material that substantially insulates against electrical and thermal energy to protect the eye.

10. A method for treating Meibomian gland dysfunction comprising the steps of:
    shielding a surface of an eye using an ocular protection device comprising a corneal shield and a handle which allows for manipulation of the corneal shield on the eye;
    heating the outside of an eyelid, using a hand-held treatment device, to a temperature to melt, soften, or loosen obstructions in Meibomian glands;
    manually applying pressure to the outer surface of the eyelid to express obstructions blocking the glands; and
    manually controlling the corneal shield, via the handle, to apply a counterforce to the applied pressure.

11. The method claim 10, wherein the eyelid is heated by one of radiofrequency energy (RF), intense pulsed light (IPL), thermal conduction, and ultrasonic vibrations.

12. The method of claim 10, wherein the pressure is in a range of about 0.5 psi to about 10 psi.

13. The method of claim 10, wherein the pressure is applied in strokes toward the lid margin.

14. The method of claim 10, further comprising measuring the temperature of the eyelid using at least one temperature sensor, the temperature sensor selected from a group consisting of an infrared temperature sensor, a fiber optic sensor, a thermistor, and a thermocouple.

15. The method of claim 14, wherein the temperature sensor is located on the treatment device.

16. The method of claim 14, wherein the temperature is automatically controlled via feedback control.

17. The method of claim 10, wherein the handle of the device has a hinge which permits movement of the handle to allow access to the eyelid and to allow an operator to control the corneal shield.

18. The method of claim 17, wherein the hinge is a living hinge.

19. The method of claim 10, wherein the pressure is applied by the treatment device.

* * * * *